United States Patent
Konno et al.

(10) Patent No.: US 9,247,914 B2
(45) Date of Patent: Feb. 2, 2016

(54) X-RAY IMAGING APPARATUS AND X-RAY FOCUS POSITION CONTROL METHOD OF X-RAY IMAGING APPARATUS

(75) Inventors: Yasutaka Konno, Tokyo (JP); Takashi Ishikawa, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 420 days.

(21) Appl. No.: 13/822,822

(22) PCT Filed: Sep. 11, 2011

(86) PCT No.: PCT/JP2011/070657
§ 371 (c)(1),
(2), (4) Date: Mar. 13, 2013

(87) PCT Pub. No.: WO2012/043199
PCT Pub. Date: Apr. 5, 2012

(65) Prior Publication Data
US 2013/0177130 A1    Jul. 11, 2013

(30) Foreign Application Priority Data
Sep. 29, 2010    (JP) .............................. 2010-219464

(51) Int. Cl.
*A61B 6/08*  (2006.01)
*A61B 6/03*  (2006.01)
*H05G 1/52*  (2006.01)

(52) U.S. Cl.
CPC . *A61B 6/032* (2013.01); *A61B 6/08* (2013.01); *H05G 1/52* (2013.01)

(58) Field of Classification Search
CPC ........ A61B 6/032; A61B 6/08; A61B 6/4021; A61B 6/06; H05G 1/52; G21K 1/04
See application file for complete search history.

(56) References Cited

U.S. PATENT DOCUMENTS

| 5,566,220 | A | 10/1996 | Saito et al. |
| 6,215,844 | B1 | 4/2001 | Adachi et al. |
| 6,322,248 | B1 | 11/2001 | Yanagita et al. |
| 2010/0119039 | A1 * | 5/2010 | Miller et al. .................... 378/62 |

FOREIGN PATENT DOCUMENTS

| EP | 1121899 A1 | 8/2001 |
| JP | 6-169914 | 6/1994 |

(Continued)

OTHER PUBLICATIONS

International Search Report in PCT/JP2011/070657.

*Primary Examiner* — David J Makiya
*Assistant Examiner* — John Corbett
(74) *Attorney, Agent, or Firm* — Cooper & Dunham LLP

(57) ABSTRACT

An X-ray imaging apparatus including: X-ray generation means that irradiates X-rays from the focus and that has a first portion changing so as to have a first change component and a second portion changing so as to have a second change component, which is different from the first change component; focus position detection means that detects a focus position when the X-rays are irradiated; focus position change amount estimation means that estimates the amount of change in the focus position at an arbitrary point of time with respect to the reference position of the focus using a first amount of change, which changes so as to have the first change component, and a second amount of change, which changes so as to have the second change component; and correction means that corrects the positions of the irradiation region of the X-rays so as to cancel the amount of change in the focus position estimated by the focus position change amount estimation means.

14 Claims, 20 Drawing Sheets

(56) References Cited

FOREIGN PATENT DOCUMENTS

| JP | 2000-51201 | 2/2000 |
| JP | 2000-51209 | 2/2000 |
| JP | 2002-319359 | 10/2002 |
| JP | 2010-524619 | 7/2010 |

* cited by examiner

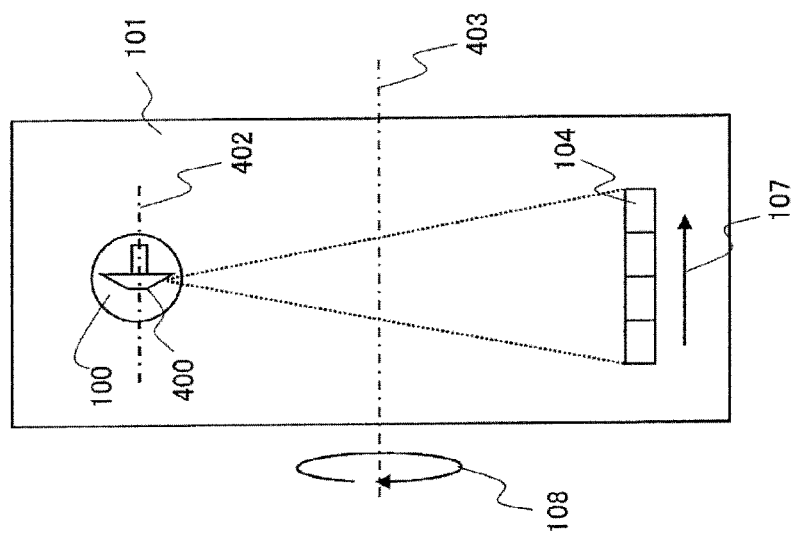

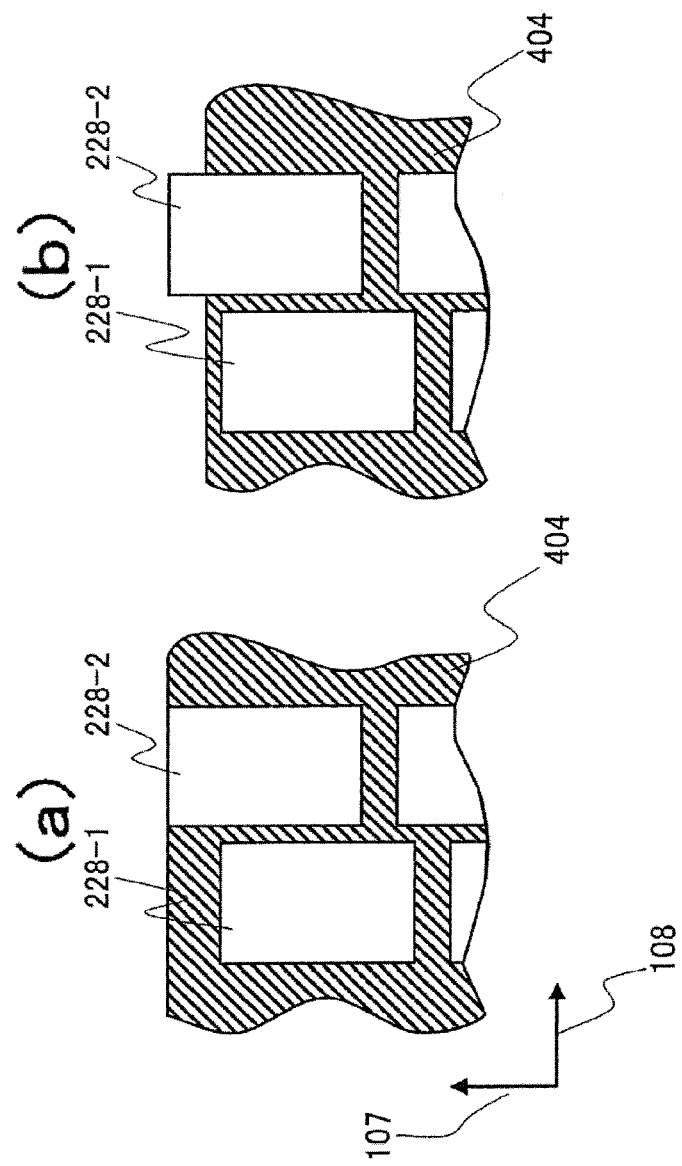

X-RAY IMAGING APPARATUS AND X-RAY FOCUS POSITION CONTROL METHOD OF X-RAY IMAGING APPARATUS

TECHNICAL FIELD

The present invention relates to an X-ray imaging apparatus and in particular, to an X-ray imaging apparatus that corrects a change in the focus position of X-rays and an X-ray focus position control method of the X-ray imaging apparatus.

BACKGROUND ART

The X-ray CT apparatus is an apparatus that acquires a tomographic image (hereinafter, described as a reconstructed image) of an object by calculating an X-ray absorption coefficient from an X-ray transmission image (hereinafter, described as projection data) of the object imaged from a plurality of directions. The X-ray CT apparatus is widely used in the medical or non-destructive inspection field. In particular, increasing the speed of rotational driving or arranging X-ray detectors in multiple stages in a rotation axis direction is in progress in the medical field in recent years. In this manner, it has been possible to image the whole of moving organs, such as the heart, without causing blurring.

An X-ray tube used as an X-ray source in these X-ray CT apparatuses generates X-rays by accelerating thermal electrons, which are generated by the filament, with a high voltage while making the thermal electrons converge on the focus and collide with the rotating anode target. In this case, some of the energy of the thermal electrons is converted into X-rays, but most of the energy of the thermal electrons is converted into heat. Accordingly, the temperature at the focus becomes high. Due to this heat, the temperature of the rotary shaft that supports the X-ray target is increased and this causes expansion and contraction (hereinafter, referred to as thermal expansion). As a result, the focus position changes. Then, since the generated heat is directed to the outside by radiation or a cooler, the temperature of the rotary shaft of the X-ray target or the like falls. Since this causes a contraction, the focus position changes again. In many X-ray CT apparatuses, as shown in FIG. 19, a rotary shaft 402 of an X-ray target 400 in an X-ray tube 100 is disposed such that the direction of the rotary shaft 402 matches the direction of a rotary shaft 403 of a gantry rotation unit 101, and this direction matches a slice direction 107 of an X-ray detector 104. Therefore, if the focus position shifts due to the thermal expansion of the rotary shaft 402 of the X-ray target or the like occur, the X-ray irradiation range changes in the slice direction 107.

Such thermal expansion may cause the degradation of image quality, such as the occurrence of artifacts or a lowering in the quantitative capability, in a reconstructed image. This phenomenon will be described with reference to FIG. 20. FIG. 20 is an explanatory diagram showing that a change in the X-ray irradiation range becomes the cause of the occurrence of artifacts, a lowering in the quantitative capability, and the like, where FIG. 20(a) shows an example of the X-ray irradiation range and FIG. 20(b) shows an example of the X-ray irradiation range that is different from FIG. 20(a). FIG. 20 shows two X-ray detection elements 228, which are located at the end in a slice direction and are adjacent to each other in a channel direction 108, in an X-ray detector in which the X-ray detect ion elements 228 are arranged in a two-dimensional manner in the slice direction 107 and the channel direction 108. In addition, in FIGS. 20(a) and 20(b), X-ray irradiation ranges 404 are different.

There is a positional deviation in the slice direction 107 between X-ray detection elements 228-1 and 228-2 described in FIG. 20. This is because of positional deviation or deformation occurring in scintillator elements or photodiode elements which form the X-ray detection elements at the time of manufacturing or assembly, positional deviation or deformation occurring at the time of bonding or mounting of a block substrate configured to include scintillator elements or photodiode elements, positional deviation between arranged modules when an X-ray detector is formed by a plurality of X-ray detection modules, or the like.

It is difficult to completely eliminate such positional deviation.

Thus, when there is a positional deviation in the slice direction between the X-ray detection elements 228, the X-ray detection elements 228-1 and 228-2 show different changes if the irradiation range moves in the slice direction 107 from FIG. 20(a) to FIG. 20(b). In the X-ray detection element 228-1, the output does not change since X-rays are incident on the entire X-ray detection element in both the cases shown in FIGS. 20(a) and 20(b). On the other hand, in the X-ray detection element 228-2, in the case shown in FIG. 20(b), the output is reduced since X-rays do not strike apart of the X-ray detection element. Such an output change that differs depending on the X-ray detection element 228 causes the occurrence of artifacts or a lowering in the quantitative capability in a reconstructed image.

In order to prevent a change in the X-ray irradiation range due to such a focus shift, for example, as disclosed in PTL 1, an X-ray collimator is moved by estimating the focus position at the time of next X-ray irradiation using the focus position detected at the time of the last X irradiation and cooling characteristic data.

CITATION LIST

Patent Literature

[PTL 1] JP-A-2000-51209

SUMMARY OF INVENTION

Technical Problem

In the focus position estimation method disclosed in PTL 1, however, in the case of using the focus position detected at the time of the last X-ray irradiation, there is a problem in that the prediction accuracy is lowered when there is an influence of the heat due to X-rays irradiated before the last irradiation, for example, since there are a plurality of factors of thermal expansion of different temperature transmissions. For example, this happens when there are a thermal expansion portion, which becomes warmed immediately by X-ray irradiation, and a portion, which requires time to become warm, in the X-ray tube and the cooling characteristics of the portions are different. In this case, the temperature of each portion is determined depending on the conditions of X-ray irradiation before the last X-ray irradiation, the X-ray irradiation interval, or the like. Accordingly, the whole cooling characteristics change according to the situation, and the prediction accuracy is lowered. This may lower the irradiation field determination accuracy and accordingly degrade the image quality of a CT.

The present invention has been made in view of the above-described problems, and it is an object of the present invention to provide an X-ray imaging apparatus that improves the focus position prediction accuracy even if there is thermal expansion due to a plurality of factors and its control method.

Solution to Problem

In order to solve the above-described problems, an X-ray imaging apparatus according to the present invention includes: an X-ray generation unit that irradiates X-rays from a focus and that has a first portion changing so as to have a first change component and a second portion changing so as to have a second change component, which is different from the first change component, due to heat generated by the X-ray generation unit; an X-ray detection unit that detects the X-rays and converts the detected X-rays into electrical signals; a focus position detection unit that detects a focus position when the X-rays are irradiated; a focus position change amount estimation unit that estimates an amount of change in the focus position with respect to a reference position of the focus using a first amount of change, which changes so as to have the first change component, and a second amount of change, which changes so as to have the second change component; and a correction unit that corrects relative positions of an irradiation region of the X-rays and the X-ray detection unit so as to cancel the amount of change in the focus position estimated by the focus position change amount estimation unit.

In addition, an X-ray focus position control method of an X-ray imaging apparatus according to the present invention is an X-ray focus position control method of an X-ray imaging apparatus including an X-ray generation unit that irradiates X-rays from a focus and has a first portion changing so as to have a first change component and a second portion changing so as to have a second change component, which is different from the first change component, due to heat generated by the X-ray generation unit and an X-ray detection unit that detects the X-rays and converts the detected X-rays into electrical signals, and is characterized in that it includes: a step of detecting a focus position when the X-rays are irradiated; a step of estimating an amount of change in the focus position with respect to a reference position of the focus using a first amount of change, which changes so as to have the first change component, and a second amount of change, which changes so as to have the second change component; and a step of correcting relative positions of an irradiation region of the X-rays and the X-ray detection unit so as to cancel the estimated amount of change in the focus position.

Advantageous Effects of Invention

According to the present invention, when X-ray focus shift occurs due to thermal expansion factors of a plurality of portions of different temperature transmission, it is possible to eliminate and suppress the degradation of image quality due to focus shift without delaying the imaging timing by determining and changing the X-ray irradiation range accurately even if X-ray irradiation for detecting the focus position is not performed proximately.

BRIEF DESCRIPTION OF DRAWINGS

FIG. 14(a) shows a state before focus shift and FIG. 14(b) shows a case where focus shift occurs due to the heat generated by X-ray irradiation but focus shift control is not performed.
FIG. 16(a) shows a state before focus shift and FIG. 16(b) shows a case where focus shift occurs due to the heat generated by X-ray irradiation but focus shift control is not performed.
FIG. 17(a) shows a state before focus shift and FIG. 17(b) shows a case where focus shift occurs due to the heat generated by X-ray irradiation but focus shift control is not performed.
FIG. 19 is an explanatory diagram showing the direction of a rotary shaft 402 of an X-ray CT apparatus in the related art.
FIG. 20 is an explanatory diagram showing that a change in the X-ray irradiation range becomes the cause of the occurrence of artifacts in an X-ray CT apparatus in the related art, a lowering in the quantitative capability, and the like, where
FIG. 20(a) shows an example of the X-ray irradiation range and FIG. 20(b) shows an example of the X-ray irradiation range that is different from FIG. 20(a).

DESCRIPTION OF EMBODIMENTS

Figure 1:
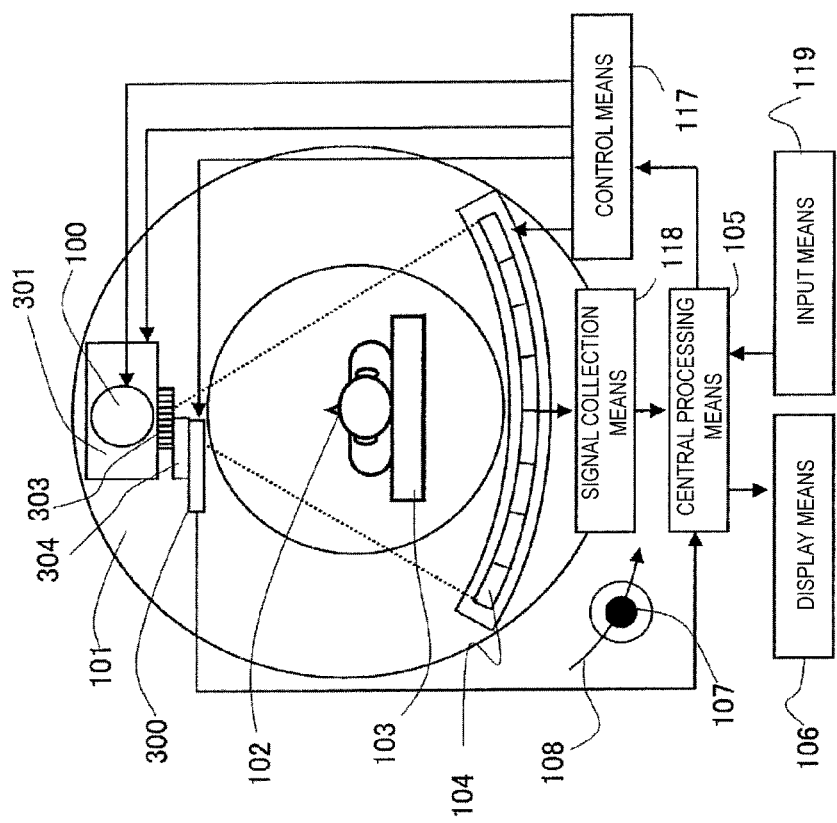
FIG. 1 is a schematic diagram of an X-ray CT apparatus according to a first embodiment.

Hereinafter, embodiments of the present invention will be described in detail with reference to the drawings. In the following explanation, components having the same functions are denoted by the same reference numerals, and repeated explanation thereof will be omitted.

First Embodiment

Figure 2:
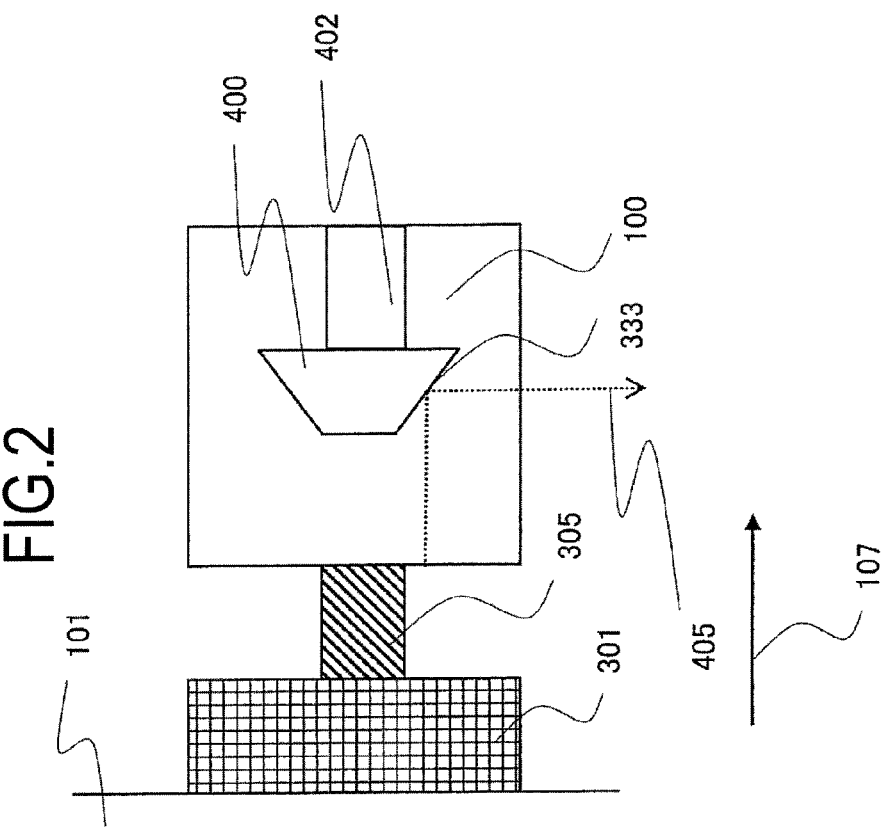
FIG. 2 is an explanatory diagram showing the positional relationship between an X-ray source 100 and X-ray tube moving means 301.
Figure 3:
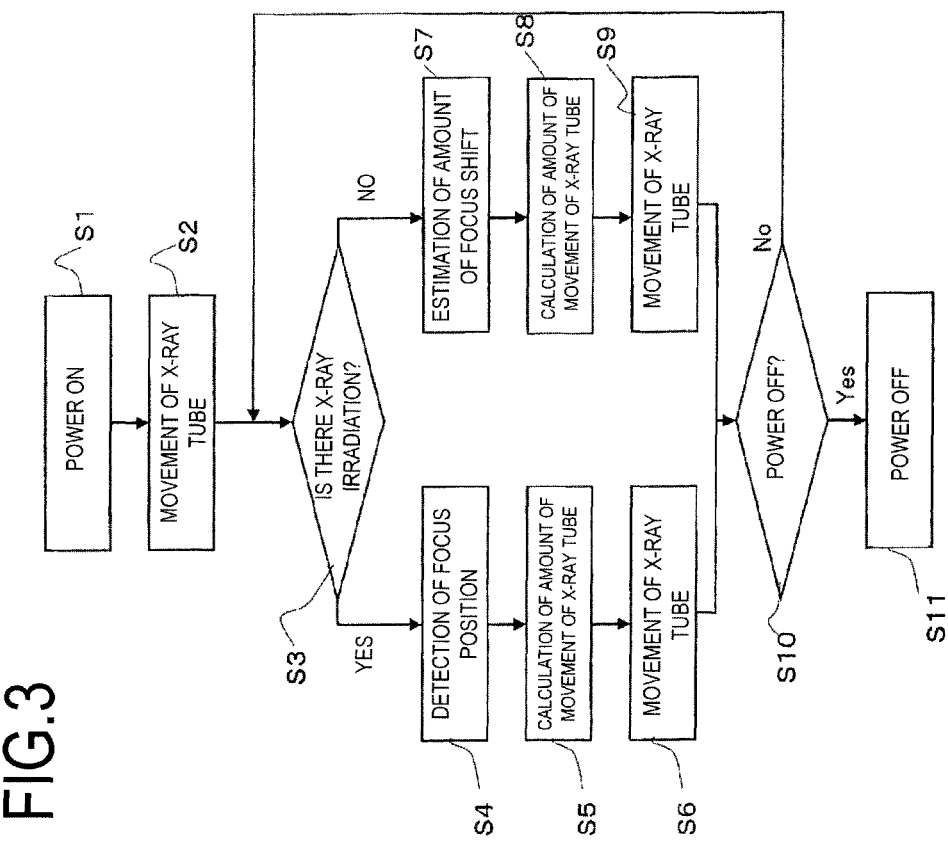
FIG. 3 is a flow chart showing the flow of focus control processing according to the present embodiment.
Figure 4:
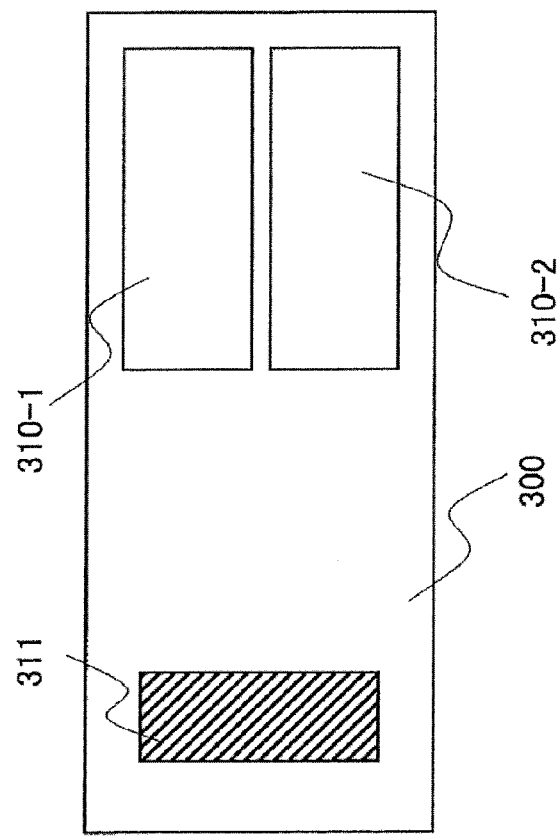
FIG. 4 is a schematic diagram of a detector for focus position measurement.
Figure 5:
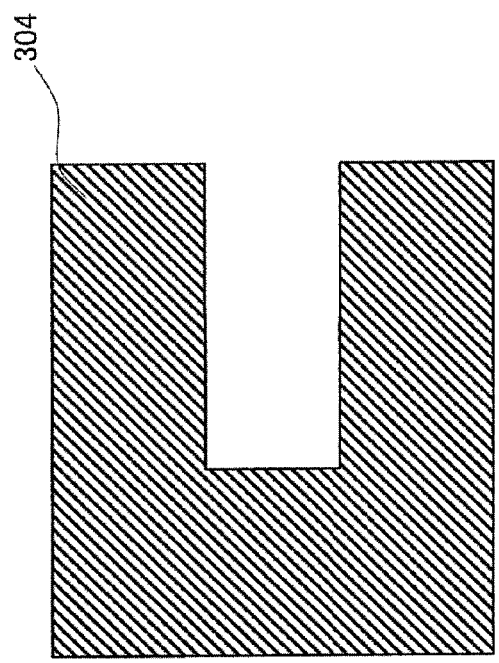
FIG. 5 is a schematic diagram of a slit for focus position measurement for detecting the focus position.
Figure 6:
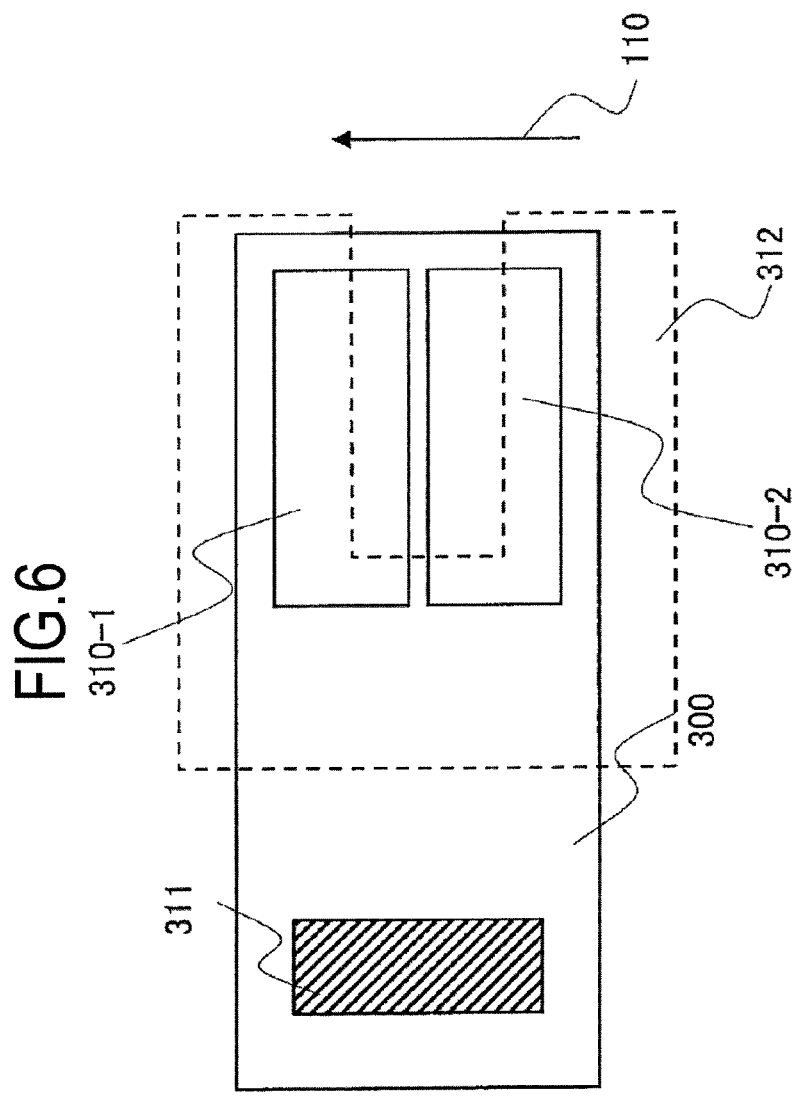
FIG. 6 is an explanatory diagram showing a focus position detection method of focus position detection means.
Figure 7:
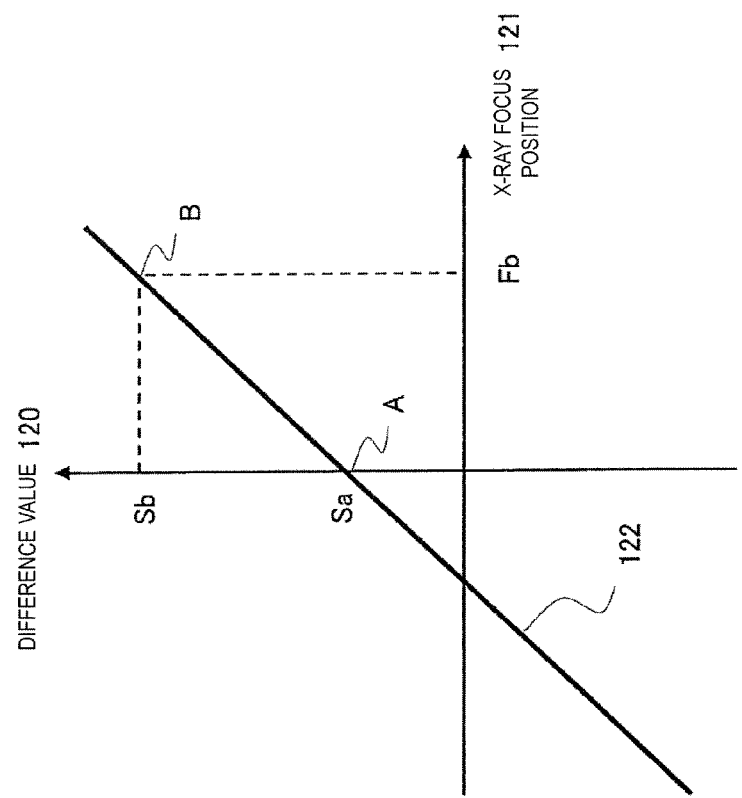
FIG. 7 is an explanatory diagram showing a method of detecting a focus position from a difference value of outputs of X-ray detection elements for focus detection.
Figure 8:
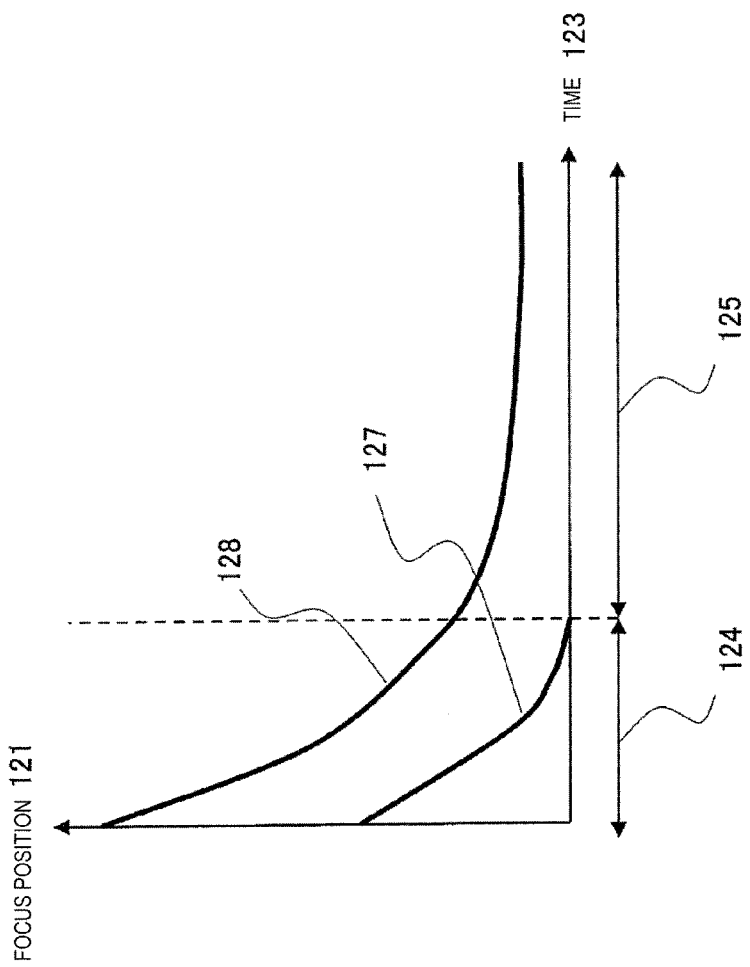
FIG. 8 is an explanatory diagram showing an example of the thermal expansion characteristics obtained by pre-measurement.
Figure 9:
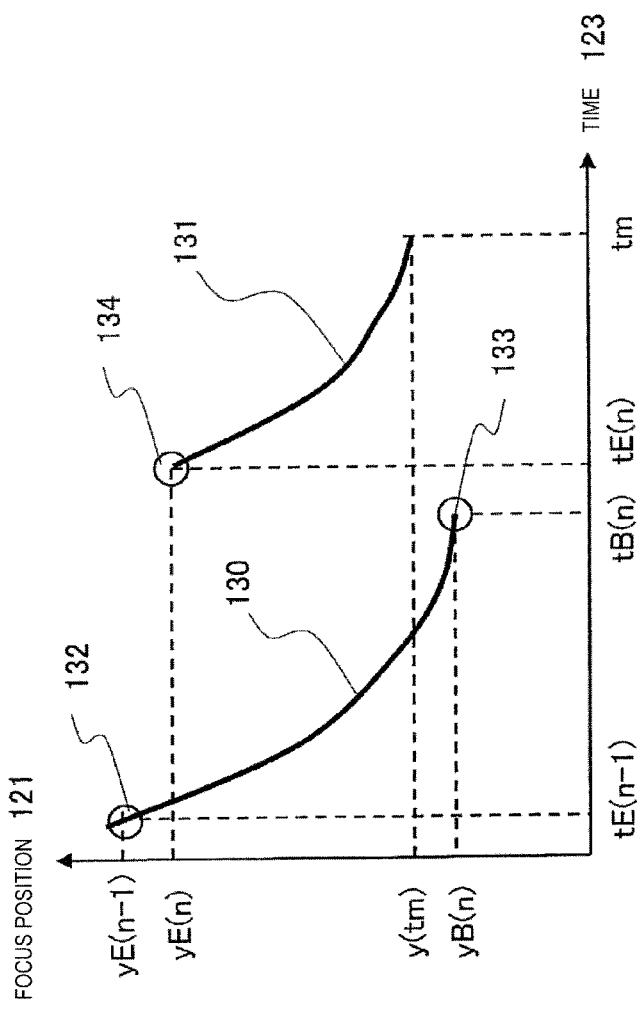
FIG. 9 is an explanatory diagram showing an example of a method of estimating the amount of focus shift.

The present embodiment is an example of an X-ray CT apparatus used in medicine, and will be described below using FIGS. 1 to 9.
FIG. 1 is a schematic diagram of an X-ray CT apparatus according to the present embodiment. FIG. 2 is an explanatory diagram showing the positional relationship between an X-ray source 100 and X-ray tube moving means 301. FIG. 3 is a flow chart showing the flow of focus control processing according to the present embodiment. FIG. 4 is a schematic diagram of a detector for focus position measurement. FIG. 5 is a schematic diagram of a slit for focus position measurement to detect a focus position. FIG. 6 is an explanatory diagram showing a focus position detection method of focus position detection means. FIG. 7 is an explanatory diagram showing a method of detecting a focus position from a difference value of outputs of X-ray detection elements for focus detection. FIG. 8 is an explanatory diagram showing an example of the thermal expansion characteristics obtained by pre-measurement. FIG. 9 is an explanatory diagram showing an example of a method of estimating the amount of focus shift.

The outline of the X-ray CT apparatus according to the present embodiment will be described using FIG. 1. The X-ray CT apparatus according to the present embodiment is configured to include the X-ray source 100, the X-ray tube moving means 301, an X-ray collimator 303, focus position detection means 306 including a slit for focus position measurement 304 and a detector for focus position measurement 300, an X-ray detector 104, signal collection means 118, a central processing unit 105, a display device 106, input means 119, control means 117, a gantry rotation unit 101, and a top panel bed 103.

The plurality of X-ray detectors 104 are arranged in an arc shape with the X-ray source 100 as the approximate center, and are mounted in the gantry rotation unit 101 together with the X-ray source 100.

Here, in order to simplify the explanation, a case where the number of X-ray detectors 104 is 8 is shown in FIG. 1. In the actual apparatus, however, the number of X-ray detectors 104 is about 40, for example. In addition, an X-ray grid (not shown in FIG. 1) is provided on the front surface (surface facing the X-ray source 100) of the X-ray detector 104 so that X-rays scattered by an object 102 or the like, among X-rays emitted from the X-ray source 100, are prevented from being incident on the X-ray detector 104.

Next, in order to describe the positional relationship between the X-ray source 100 and the X-ray tube moving means 301 and a method of moving the X-ray source 100, FIG. 2 shows a cross-sectional view in a rotation axis direction 107. The X-ray tube moving means 301 is fixed to the gantry rotation unit 101, and supports the X-ray source 100 through a support rod 305. Due to such a structure, the X-ray tube moving means 301 can move the X-ray source 100 in the rotation axis direction 107 by moving the support rod 305. On the other hand, in the X-ray source 100, an X-ray target rotation shaft 402 that rotatably supports a target 400 is provided. The place where accelerated electrons collide with the target is a focus 333 of an X-ray 405. Due to the heat due to the generation of the X-ray 405, the X-ray target rotation shaft 402 or the like thermally expands. As a result, the focus position within the X-ray source 100 moves. At the same time, thermal expansion occurs since the support rod 305 becomes warm. As a result, the X-ray source 100 moves in the rotation axis direction 107, and the focus position changes.

Next, an imaging method (hereinafter, described as actual imaging) for obtaining a cross-sectional image (reconstructed image) and a method of processing will be described with reference to FIG. 1. First, focus position control is started after powering the X-ray CT apparatus. This control method will be described in detail below. Then, when there is an input to start actual imaging from the input means 119, fan-shaped X-rays are emitted from the X-ray source 100 toward the object 102 placed on the top panel bed 103, and X-rays transmitted through the object 102 are detected by the X-ray detector 104 and are converted into electrical signals. The X-ray collimator 303 is placed in an X-ray output port of the X-ray source 100 to limit the irradiation range.

By repeatedly performing this imaging while changing the irradiation angle of the X-ray with respect to the object 102 by rotating the gantry rotation unit 101 in a rotation direction 108, projection data is obtained over the angle range of 360°. The imaging is performed every 0.4° between a plurality of views, for example. In addition, also in this period, X-ray focus position control is performed.

The electrical signals obtained in this manner are collected by the signal collection means 118 and are converted into digital signals, thereby generating raw data. Then, the central processing unit 105 performs image processing on the raw data to generate projection data. This image processing is a correction of variations in the sensitivity or offset of the X-ray detector 104, for example. Then, the projection data is reconstructed to generate a reconstructed image of the X-ray absorption coefficient distribution of the object 102. The result is displayed on the display device 106.

Next, the above-described focus position control method performed by the central processing unit 105 will be described with reference to FIG. 3.

(Step S1)
Powering (S1) of the X-ray CT apparatus is performed.
(Step S2)
The X-ray tube moving means 301 moves the X-ray tube 100 to the initial position (S2). This initial position is a focus position (hereinafter, described as an initial focus position) to realize X-ray irradiation to a predetermined X-ray irradiation range when there is no thermal expansion before the X-ray tube 100 becomes warm. This initial focus position is measured in advance of actual measurement, and is stored in storage means of the central processing means 105. Then, in this step, the X-ray tube moving means 301 reads the initial focus position from the above-described storage means and moves the X-ray source 100 to the position. In addition, the above-described predetermined irradiation range is an irradiation range whose center of the shadow of irradiated X-rays in a slice direction matches the center of the X-ray detectors 104 in the slice direction, for example.

(Step S3)
Then, the central processing means 105 determines whether or not there has been X-ray irradiation proximately (S3). Here, "proximately" is a period of time until current determination processing (processing of S3) is performed after the last determination processing (processing of S3) is performed, for example. In addition, the determination processing of step S3 may be performed every predetermined time, such as 1 second, for example. In this manner, since determination can be performed every predetermined time, real-time control can be satisfactorily performed.

When it is determined that X-ray irradiation has been performed in step S3, the process proceeds to step S4. When it is determined that X-ray irradiation has not been performed in step S3, the process proceeds to step S7.

(Step S4)
The focus position detection means 306 detects a focus position. In this case, the focus position is detected in both an initial period (hereinafter, described as an initial stage) and an end period (hereinafter, described as an end stage) within the last X-ray irradiation period that has been determined to be present in the determination of step S3. Here, the initial stage is within the first half of the X-ray irradiation period, for example, and the end stage is within the second half of the X-ray irradiation period, for example. When X-ray irradiation is performed in the actual imaging, the focus position detection means 306 detects a focus position using the value of the X-ray irradiated at that time that is detected by the detector for focus position measurement 300. Accordingly, in this step S4, the measured value of the focus position is calculated using the detection value obtained by the last X-ray irradiation. These detected focus positions in the initial stage and the end stage and the times, at which the focus positions are measured, are stored in the storage means of the central processing means 105. Details of the focus position detection method in this step will be described later.

(Step S5)

The central processing means 105 calculates the amount of movement of the X-ray tube 100 on the basis of the detected focus position result (S5). Details of the method of calculating the amount of movement of the X-ray tube 100 in this step will be described later.

(Step S6)

The control means 117 moves the X-ray tube 100 by controlling the X-ray tube moving means 301 by the amount calculated in step S5 (S6). This movement is realized when the X-ray tube moving means 301 has a mechanism for moving the X-ray tube 100 with a stepping motor and the control means 117 transmits a control signal to the stepping motor, for example.

(Step S7)

When it is determined that X-ray irradiation has not been performed in the determination processing of step S3, it is estimated by how much the focus has moved from the initial focus position (S7). Details of the focus position estimation method in this step will be described later.

(Step S8)

The central processing means 105 calculates the amount of movement of the X-ray tube 100 on the basis of the focus position estimated in step S7 (S8). Details of the method of calculating the X-ray tube 100 in this step will be described later.

(Step S9)

The control means 117 moves the X-ray tube 100 by controlling the X-ray tube moving means 301 by the amount calculated in step S8 (S9). This movement is realized when the X-ray tube moving means 301 has a mechanism for moving the X-ray tube 100 with a stepping motor and the control means 117 transmits a control signal to the stepping motor, for example.

Accordingly, even if thermal expansion occurs, it is possible to locate the actual focus at the initial focus position. When the X-ray tube moving means 301 does not perform control to move the X-ray tube 100, the actual focus is shifted from the initial focus position by the amount of focus shift obtained by estimation.

(Steps S10 and S11)

The central processing means 105 performs determination 167 regarding whether or not to turn the power OFF (S10). When the determination is No, the process returns to the processing of step S2 for determining whether or not there is X-ray irradiation. When the determination is Yes, the power of the X-ray CT apparatus is turned OFF (S11).

Then, methods of detection (S4) of a focus position and calculation (S5) of the amount of movement of the X-ray tube 100, which have been described previously, will be described in detail.

The focus position detection means 306 detects a focus position using X-rays in actual imaging. The focus position detection means 306 is configured to include the detector for focus position measurement 300 shown in FIG. 4, for example, and the slit for focus position measurement 304 shown in FIG. 5, for example. The detector for focus position measurement 300 has, for example, two X-ray detection elements for focus detection 310-1 and 310-2, and the output is output from a connector 311. As a result, the central processing means 105 obtains the data. For example, the slit for focus position measurement 304 is formed of metal with large X-ray absorption, such as tungsten, molybdenum, lead, and brass. The focus position detection means 306 has a structure where the slit for focus position measurement 304 is provided at a position slightly distant from the X-ray incidence surface of the detector for focus position measurement 300, and a shadow 312 shown in FIG. 6 is generated on the detector for focus position measurement 300 when X-rays are irradiated.

When the X-ray focus moves in the slice direction 107, this shadow 312 moves in a direction 110, and the size of an overlapping region of the shadow 312 and the X-ray detection elements for focus detection 310-1 and 310-2 changes. For example, when the slit for focus position measurement 304 moves to the positive side of the direction 110, the shadow 312 also moves similarly. As a result, the X-ray incidence area of the X-ray detection element for focus detection 310-1 increases depending on the amount of movement, and the X-ray detection element for focus detection 310-2 decreases on the contrary. When the slit 304 moves to the negative side of the direction 110, the above is reversed. Therefore, for example, a difference value of the outputs of the X-ray detection elements for focus detection 310-1 and 310-2 reflects the amount of movement of the X-ray focus position.

FIG. 7 shows an example of the relationship between the difference value and the amount of movement. A function 122 is an example of the result obtained by measuring the outputs of the X-ray detection elements for focus detection 310-1 and 310-2 while changing the X-ray focus position 121 by moving the X-ray tube 100 in advance of actual imaging, and the difference value 120 is stored in the storage means of the central processing means 105. The horizontal axis indicates the amount of movement 121 of the X-ray focus, and the vertical axis indicates the difference value 120 of the output. In addition, there is a point A when realizing a predetermined irradiation range, and the difference value at this time is $S_a$.

In actual imaging, the central processing means 105 calculates how much the X-ray tube 100 should be moved from the difference value 120 of the X-ray detection elements for focus detection 310-1 and 310-2 and the stored function 122. For example, it is assumed that the difference value of the outputs of the X-ray detection elements for focus detection 310-1 and 310-2 used in actual imaging is $S_b$. The central processing means 105 acquires the difference value $S_b$ and calculates a point B, which indicates the difference value $S_b$ on the function 122, by applying the difference value $S_b$ to the function 122 shown in FIG. 7. The focus position Fb at the point B is a current focus position. The central processing means 105 recognizes that the current focus position is located at a position shifted from the initial focus position (point A) by Fb. Therefore, the central processing means 105 calculates, as $-F_b$, the amount of movement of the X-ray tube 100 for correcting the amount of movement of the focus position from the initial focus position to the current focus position.

Then, a method of estimating the amount of focus shift described in step S7 and a method of calculating the amount of movement of the X-ray tube for correcting the amount of focus shift estimated in step S8, which are shown in FIG. 3, will be described.

In order to estimate the amount of focus shift, in advance of actual imaging, a change in focus position at the time of cooling is evaluated in a state where control to move the X-ray tube 100 is not performed by the X-ray tube moving means 301.

In this pre-measurement, both the focus shift within the X-ray tube 101 occurring after heating generated by X-ray irradiation and the focus shift due to the contraction of the support rod 305 are evaluated, and a time constant $\tau_1$ of the focus shift within the X-ray tube 101 and a time constant $\tau_2$ of the change in the support rod 305 are determined and stored in the storage means of the central processing means 105. Here, since the focus shift within the X-ray tube 101 is caused by thermal expansion of the X-ray target rotation shaft 402 or the like as described above, the X-ray target rotation shaft 402 or the like contracts immediately due to cooling after thermal expansion immediately after heating. On the other hand, the contraction of the support rod 305 occurs since the heat from the X-ray tube 101 is slowly transmitted to expand the support rod 305 and then the heat escapes slowly from the hot bath. Therefore, in general, the time constant $\tau_2$ is larger than the time constant $\tau_1$. In addition, the change in the support rod 305 occurs when a large amount of overheating occurs due to X-rays.

As an evaluation method, for example, focus shift characteristics when causing only the focus shift within the X-ray tube 101 and when causing both the focus shift within the X-ray tube 101 and the focus shift due to the support rod 305 are acquired by changing the amount of heating, thereby obtaining each time constant. For example, when the amount of heating is small, the support rod 305 is away from the X-ray focus at which heat is generated. Accordingly, the support rod 305 does not warm up enough, causing only the approximate focus shift within the X-ray tube 101. On the other hand, when the amount of heating is large, both become warm to cause a focus shift.

FIG. 8 shows an example of the result obtained as described above. The horizontal axis indicates elapsed time 123 after stopping X-ray irradiation for heating, and the vertical axis indicates the obtained focus position 121 and zero on this vertical axis indicates an initial focus position. A curve 127 shows an example of the result when a small amount of X-rays for heating are irradiated, and a curve 128 shows an example when a large amount of X-rays for heating are irradiated. In this example, the curves 127 and 128 attenuate with the same time constant in a period range 124. In a period range 125, however, attenuation of different components is seen only in the curve 128. The change in the period range 125 can be regarded as a change in the support rod 305, while the change in the period range 124 can be regarded as a focus shift within the X-ray tube 101.

Here, the focus shift within the X-ray tube 101 also needs to occur with a small amount of X-rays for heating. Therefore, irradiation is performed for a short time (for example, several seconds) using a large tube current (for example, 500 mA). In addition, in the case of a large amount of X-rays for heating, irradiation of a relatively long time (for example, several seconds) is intermittently performed multiple times for about 30 minutes using a large tube current (for example, 500 mA). On the other hand, even after heating by X-rays, it is necessary to irradiate X-rays in order to measure the focus position. In this case, in order to determine the time constant accurately, it is necessary to reduce heating by X-rays. For this reason, a focus is obtained by irradiating a small tube current (for example, 10 mA) for a short time (for example, 0.5 second). In addition, it is also necessary to set the measurement interval to be sufficiently large compared with the irradiation time.

Then, the time constant of each component is determined from the measurement result, and the result is stored in the storage means of the central processing means 105. The time constant is determined by fitting the obtained curve, for example. In the case of the result shown in FIG. 8, for example, the time constant $\tau_1$ of the focus shift within the X-ray tube 101 is determined by performing fitting using a function of expression (1) for the result of the curve 127, and the time constant $\tau_2$ of the change in the support rod 305 is determined by performing fitting using a function of expression (2) for the result of the curve 128. These determined time constants are stored in the storage means of the central processing means 105. Here, y is the focus position 121, t is elapsed time from X-ray irradiation, and A, B, and C are constants indicating the size of the amplitude.

$$y = A\exp\left(-\frac{t}{\tau_1}\right) \quad \text{Expression (1)}$$

$$y = B\exp\left(-\frac{t}{\tau_1}\right) + C\exp\left(-\frac{t}{\tau_2}\right) \quad \text{Expression (2)}$$

Using the focus position and the characteristic parameters $\tau_1$ and $\tau_2$ stored in the storage means of the central processing means 105 as described above, the amount of focus shift of each component is estimated in the estimation of the amount of focus shift in actual imaging (step S7 in FIG. 3). An example of the estimation method will be described with reference to FIG. 9. In FIG. 9, the focus position y(tm) at time tm is estimated by an estimation function using expression (2). Here, the value of a detection result 132 of the focus position in the end stage of the before-last X-ray irradiation is yE(n−1) and the time is tE(n−1), the value of a detection result 133 of the focus position in the initial stage of the last X-ray irradiation is yB(n) and the time is tB(n), and curves 130 and 131 show results of the estimation function. Here, the value of the focus position 121 is a converted value in a state where movement control by the X-ray tube moving means 301 is not performed.

In order to estimate the focus position y(tm), the estimation function 130 is first determined using results of the detection result 132 in the end stage of the before-last X-ray irradiation and the detection result 133 in the initial stage of the last X-ray irradiation. This is obtained by solving the result when both measurement points with the time tE(n−1) as a reference are substituted into expression (2). Accordingly, it can be seen that the coefficients B and C are determined as in expression (3).

$$C = \frac{yB(n) - yE(n-1)\exp\left(-\frac{tB(n) - tE(n-1)}{\tau_1}\right)}{\exp\left(-\frac{tB(n) - tE(n-1)}{\tau_2}\right) - \exp\left(-\frac{tB(n) - tE(n-1)}{\tau_1}\right)} \quad \text{Expression (3)}$$

$$B = yE(n-1) - \frac{yB(n) - yE(n-1)\exp\left(-\frac{tB(n) - tE(n-1)}{\tau_1}\right)}{\exp\left(-\frac{tB(n) - tE(n-1)}{\tau_2}\right) - \exp\left(-\frac{tB(n) - tE(n-1)}{\tau_1}\right)}$$

Then, the curve 131 is calculated. In this case, the coefficient C is calculated on the assumption that the amount of change in the support rod 305 of the estimation function 130 shown in expression (3) continues until time tm. That is, the coefficient C is calculated on the assumption that a change in the support rod 305 caused by X-ray irradiation between time tB(n) and time tE (n) is so small as to be neglected. This is true in general when a change in the support rod 305 is not sensitive to single X-ray irradiation, when a change in the support rod 305 slowly changes with time delay, when an interval between time tm and time tE(n) is shorter than the delay, and the like.

In this case, the coefficient C of the estimation function 131 can be calculated as an estimate at time tE(n) of the estimation function 130. Accordingly, the coefficient C of the estimation function 131 can be written as in expression (4).

$$C = \frac{yB(n) - yE(n-1)\exp\left(-\frac{tB(n)-tE(n-1)}{\tau_1}\right)}{\exp\left(-\frac{tB(n)-tE(n-1)}{\tau_2}\right) - \exp\left(-\frac{t(tB(n)-tE(n-1)}{\tau_1}\right)} \exp\left(-\frac{tE(n)-tE(n-1)}{\tau_2}\right) \quad \text{Expression (4)}$$

On the other hand, the coefficient B of the estimation function 131 is different from the value of the estimation function 130, that is, the coefficient B in expression (3). This is because the focus shift within the X-ray tube 101 occurs instantaneously with X-ray irradiation between time tB(n) and time tE(n) and this is not negligible. In this case, the coefficient B is written as in expression (5), from the detection result 134 in the end stage of the last X-ray irradiation and the coefficient C in expression (4), when calculated using expression (2) indicating the focus shift within the X-ray tube 101. Therefore, the estimate y(tm) at time tm can be determined as in expression (6).

$$B = yE(n) - C \quad \text{Expression (5)}$$

$$= yE(n) - \frac{yB(n) - yE(n-1)\exp\left(-\frac{tB(n)-tE(n-1)}{\tau_1}\right)}{\exp\left(-\frac{tB(n)-tE(n-1)}{\tau_2}\right) - \exp\left(-\frac{tB(n)-tE(n-1)}{\tau_1}\right)} \exp\left(-\frac{tE(n)-tE(n-1)}{\tau_2}\right)$$

$$y(tm) = \left[ yE(n) - \frac{yB(n) - yE(n-1)\exp\left(-\frac{tB(n)-tE(n-1)}{\tau_1}\right)}{\exp\left(-\frac{tB(n)-tE(n-1)}{\tau_2}\right) - \exp\left(-\frac{tB(n)-tE(n-1)}{\tau_1}\right)} \exp\left(-\frac{tE(n)-tE(n-1)}{\tau_2}\right) \right] \exp\left(-\frac{tm-tE(n)}{\tau_1}\right) + \frac{yB(n) - yE(n-1)\exp\left(-\frac{tB(n)-tE(n-1)}{\tau_1}\right)}{\exp\left(-\frac{tB(n)-tE(n-1)}{\tau_2}\right) - \exp\left(-\frac{tB(n)-tE(n-1)}{\tau_1}\right)} \exp\left(-\frac{tE(n)-tE(n-1)}{\tau_2}\right) \exp\left(-\frac{tm-tE(n)}{\tau_2}\right) \quad \text{Expression (6)}$$

When X-rays are irradiated after time tm, the coefficients B and C of the estimation function 131 are calculated again from the newly detected focus position and the result yE(n) at time tE(n) in the same manner as when the estimation function 130 is determined. In this case, since the coefficient C is calculated from the detection result (focus position y(tm) at time tm) in the newly detected end stage and the detection result at time 134, the coefficient C is a value including at least a part of the influence of X-ray irradiation between time tB(n) and time tE(n). Therefore, for the change in the support rod 305, only a change due to nearby X-ray irradiation, such as the last X-ray irradiation, is neglected, and the influence of the X-ray irradiation neglected is not accumulated.

As described above, this estimation can improve the estimation accuracy by taking the change in the support rod 305 into consideration. In particular, when the change in the support rod 305 is a main cause of the focus shift, for example, when estimating the focus position when time equal to or greater than the time constant $\tau_1$ and equal to or less than about several times the time constant $\tau_2$ passes from the last X-ray irradiation, the estimation accuracy is greatly improved compared with a case where the change in the support rod 305 is not taken into consideration.

Next, a method of calculating the amount of movement of the X-ray tube 100, which has been described in step S8 of FIG. 3, will be described.

In the X-ray tube movement amount calculation processing described in step S8 of FIG. 3, the amount of movement of the X-ray tube 101 is determined from the amount determined in the estimation of the amount of focus shift in step S7. In this case, when focus position control has not been performed previously, that is, when the focus position is the initial focus position, the amount of movement is −y(tm). This means that the focus position has moved by y(tm) in the opposite direction of the direction of focus shift. On the other hand, when focus position control has been performed previously, that is, when the focus position is not the initial focus position, a difference between the focus position reached by X-ray tube movement (X-ray tube movement processing by step S6 and/or step S9) until the last X-ray irradiation and y(tm) is preferably set as the amount of movement.

In order to determine the focus position reached as a result of such focus control, it is necessary to provide means for calculating or detecting the amount of movement of the X-ray tube moving means 301, for example. As an example of the means for calculating the amount of movement, it is preferable that the control means 117 have a function of recording the total amount of movement performed by the X-ray tube moving means 301. As this method, for example, when the movement of the X-ray tube moving means 301 is realized by a stepping motor and the amount of movement and a direction are determined by two types of pulse numbers of forward movement and backward movement, a sum of each pulse number is recorded, and the amount of movement of the focus can be calculated from this pulse number.

As described above, by the focus position control according to the present embodiment, a predetermined position (initial focus position) can be set as an actual focus position using the focus position information detected by X-rays when there is X-ray irradiation and using a focus position estimation result when there is no X-ray irradiation. As a result, it is possible to irradiate X-rays to the predetermined irradiation range. In particular, in the estimation of a focus position when there is no X-ray irradiation, the estimation accuracy can be improved when there is a thermal expansion component that does not change instantaneously due to X-ray irradiation or when it is not sensitive to single X-ray irradiation. In this case, it is possible to determine and change the X-ray irradiation range accurately. Therefore, even if an X-ray focus shift occurs due to a plurality of factors, it is possible to eliminate and suppress the degradation of image quality, such as the occurrence of artifacts or a lowering of the quantitative capability due to focus shift. In addition, since it is not necessary to perform X-ray irradiation for detecting the focus position proximately, delay of the imaging timing also does not occur.

Although the case where the focus positions in the initial stage and the end stage and the time at which these are measured are stored in the storage means of the central processing means 105 has been described in the present embodiment, it is needless to say that information other than the information used in prediction of the focus position, that is, information other than the detection results in the initial stage and the end stage of the last X-ray irradiation, the detection result in the end stage of the before-last X-ray irradiation, and the time information of these may be eliminated. Although the case where the calculation for focus position estimation is performed at a time at time tm has been described in the present embodiment, this is an example and does not limit the present invention. When X-rays are detected at time tB(n), the calculation of the coefficient C, that is, the calculation of expression (3) may be performed. In this case, it is needless to say that the detection result in the end stage of the before-last X-ray irradiation, the detection result in the initial stage of the last X-ray irradiation, and the time information of these may be eliminated by storing the calculation result in the storage means of the central processing means 105.

Although the case of the focus shift within the X-ray tube 101 and the focus shift due to the change in the support rod 305 has been described in the present embodiment, this is an example and does not limit the present invention. The present invention is not limited to the case of thermal expansion, and may be applied to a case where there are first and second thermal expansion, the first thermal expansion occurs immediately due to the influence of a single X-ray irradiation, and the second thermal expansion depends on the total amount of radiation and the total amount of cooling and accordingly does not occur immediately due to the influence of the single X-ray irradiation or a case where the influence of the single X-ray irradiation is small. The present embodiment is just an example where the first thermal expansion is a focus shift within the X-ray tube 101 and the second thermal expansion is a change in the support rod 305. In addition, this is the same as in subsequent embodiments.

Although the case where the initial stage and the end stage, which are periods in which the focus position is detected, are set within imaging of one rotation has been described in the present embodiment, this is an example and does not limit the present invention. For example, when performing imaging of a plurality of rotations at a time, the focus position may be detected on the assumption that a period of rotation of the first half is the initial stage and a period of rotation of the second half is the end stage. Here, it is preferable to set the initial stage to the time close to the start of X-ray irradiation and the end stage to the time close to the end. In addition, in this case, a period for which no X-ray is irradiated may be present during the imaging of a plurality of rotations.

Although the case where the focus shift within the X-ray tube 101 occurs with one time constant has been described in the present embodiment, this is an example and does not limit the present invention. A case where the focus shift within the X-ray tube 101 occurs with a plurality of time constants is also possible. In this case, it is necessary to determine and store the ratio of the amplitude of each component by prior evaluation. In addition, this is the same for the focus shift due to the change in the support rod 305.

Although the focus position estimation (step S7 in FIG. 3) and the X-ray tube movement (step S8 in FIG. 3), which are performed when there is no X-ray irradiation, have been performed at every predetermined time in the present embodiment, this is an example and does not limit the present invention. For example, the focus position estimation and the X-ray tube movement may be performed every specific number of Views in synchronization with imaging. In addition, according to the presence or absence of X-ray irradiation or the X-ray tube movement amount, time to the next determination processing (step S2 in FIG. 3) may be changed. In addition, the focus position estimation and the X-ray tube movement may be performed when there is an input of imaging standby through the input means 119. When there is an input to start the X-ray irradiation, the focus position estimation and the X-ray tube movement may be performed immediately before the X-ray irradiation.

When estimating the amount of focus shift in the present embodiment, the amount of focus shift is estimated using a function expressed by a sum of exponential functions given in expression (2). However, this is an example and does not limit the present invention. For example, it is also possible to use a function expressed by a sum of various functions, such as a power function. In addition, although the amount of movement of the X-ray tube 101 is determined on the basis of the estimated amount of focus shift, this is an example and does not limit the present invention. For example, it is also possible to determine the moving speed of the X-ray tube 101. As an example of the method, the speed is determined from a function obtained by performing time differential of expression (2). In this case, since the moving speed changes with time, it is desirable to estimate the speed at relatively short intervals.

In the present embodiment, as shown in FIG. 1, the detector for focus position measurement 300 is placed near the X-ray source 100. However, this is an example and does not limit the present invention. For example, the detector for focus position measurement 300 may be placed at any position, such as a position near the X-ray detector 104, a position between the X-ray source 100 and the X-ray detector 104, and a position that is more distant from the X-ray source 100 than the X-ray detector 104 is. In addition, it is also possible to use a part of the X-ray detector 104, such as an end of the X-ray detector 104. In this case, since it is not necessary to adjust the positional relationship between the detector for focus position measurement 300 and the X-ray detector 104, the number of works can be reduced.

Although the case where the focus is moved by moving the X-ray tube 100 using the X-ray tube moving means 301 has been described in the present embodiment, this is an example and does not limit the present invention. When the X-ray tube 100 is a mechanism that generates X-rays using an electron beam, it is also possible to move the focus position using an electrical field, a magnetic field, or the like as in the technique of flying focus, for example.

Although the coefficient C is determined from the focus detection result of the before-last end stage and the result of the last initial stage in the present embodiment, this is an example and does not limit the present invention. For example, the coefficient C may also be determined from the detection result in the end stage of n-th X-ray irradiation and the detection result in the initial stage of (n+1)-th X-ray irradiation before the before-last X-ray irradiation. This may be a method of determining the coefficient B when performing estimation using the coefficient C estimated in the past estimation. In the case of such determination, it is necessary to determine the coefficient in consideration of attenuation of the first term in expression (2), which occurs in a time $\Delta t_1$ from the time of X-ray irradiation of the n-th end stage to the time of the end stage of the last X-ray irradiation.

For example, the coefficient C determined from the detection result in the end stage of n-th X-ray irradiation and the detection result in the initial stage of (n+1)-th X-ray irradiation before the before-last X-ray irradiation is multiplied by the amount of attenuation exp(−Δt$_1$/τ$_1$), and the result is set as the coefficient C used in the estimation. Thus, when the coefficient C estimated in the past is stored and the current coefficient C is estimated using the coefficient C estimated in the past, the storage means does not need to store the detection result in the end stage of the n-th X-ray irradiation and the detection result in the initial stage of the (n+1)-th X-ray irradiation. Accordingly, large storage means is not necessary.

In addition, as described previously, not only determining the coefficient C using two detection results obtained by X-ray irradiation before the last X-ray irradiation but also determining the coefficient C using three or more detection results or one detection result is possible. Similarly, it is needless to say that one or more of the various detection results before last X-ray irradiation may be used for the coefficient B.

Although the coefficient C is determined from the focus detection result in the end stage of the before-last X-ray irradiation and the result in the initial stage of the last X-ray irradiation and the coefficient B is determined from the result of the coefficient C and the result in the end stage of the last X-ray irradiation in the present embodiment, this is an example and does not limit the present invention. For example, when the focus position detected at the time of last X-ray irradiation is located in a predetermined range, a method of setting a component of either the focus shift within the X-ray tube 101 or the movement by the support rod 305 to zero to determine the other coefficients B and C is also possible. For example, when it can be regarded that the focus position detected at the time of last X-ray irradiation is equal to or less than a certain amount of thermal expansion, the amount of heat added is small, and the focus shift due to the support rod 305 is small, the coefficient C is set to zero and only the coefficient B is calculated. In this case, for example, as described previously, the coefficient B is calculated from the result obtained by the last focus detection.

In addition, when a certain amount of expansion is exceeded and the focus shift due to the support rod 305 can be regarded as a main focus shift in an apparatus or the like in which the focus shift due to the support rod 305 is sufficiently larger than the focus shift within the X-ray tube 101, the coefficient C is assumed to be zero and only the coefficient C is calculated. In this case, for example, as described previously, the coefficient C is calculated from the focus detection result of the before-last end stage and the result of the last initial stage.

In addition, for example, the coefficient C may be determined using only the data after time has passed according to the degree at which the focus shift within the X-ray tube 101 can be regarded as zero, that is, the degree at which the term (first term on the right side) of the coefficient B in expression (2) can be regarded as zero. In this case, the degree at which the focus shift within the X-ray tube 101 is sufficiently small is when a focus position change due to X-rays returns to the same degree as the accuracy of predictive control, for example. In this case, the irradiation interval Δt$_B$ can be described as in expression (7) assuming that the required accuracy is W.

$$\Delta t_B = \tau_1 \ln\left(\frac{B}{W}\right)$$ Expression (7)

From this expression (7), for example, when the required accuracy is 100 μm, the coefficient B in last X-ray irradiation is 200 μm, and the time constant τ$_1$ is 20 minutes, the irradiation interval Δt$_B$ is calculated as about 14 minutes.

As a specific method of realizing this, the irradiation interval Δt$_B$ is determined in advance and stored in the storage means of the central processing means 105. Then, among focus position results detected in the initial stage of X-ray irradiation stored similarly, the most recent measurement result in conditions where the interval of irradiation time is equal to or greater than Δt$_B$, which is similarly stored, is extracted. In this way, the above can be realized. In addition, it is also possible to measure an X-ray irradiation interval and replace the coefficient C with a focus position result in the initial stage that is measured when the irradiation interval is equal to or greater than Δt$_B$. After determining the coefficient C in this manner, the coefficient B is calculated using a result of X-ray irradiation (time tE (n) in FIG. 9) of the latest end stage, and the estimation function expression (2) is determined.

As a method other than the method of determining the coefficients B and C described in the present embodiment, for example, the coefficients B and C may be calculated by setting the coefficient B to zero when the focus position detected at the time of the last X-ray irradiation is equal to or greater than a certain value and setting the coefficient C to zero when the focus position detected at the time of the last X-ray irradiation is equal to or less than the certain value so that the number of coefficients is always 1.

In addition, a coefficient to be set to zero may be changed according to a time constant, which is calculated from the result 132 in the before-last end stage and the result 133 in the last initial stage, instead of the focus position detected at the time of the last X-ray irradiation. In the case shown in FIG. 9, it is possible to determine a time constant τ$_3$ using expression (8) and to set the coefficient C to zero when the time constant τ$_3$ is close to τ$_1$ and set the coefficient B to zero when the time constant τ$_3$ is close to τ$_2$.

$$yB(n) = yE(n-1)\exp\left(-\frac{tB(n)-tE(n-1)}{\tau_3}\right)$$ Expression (8)

By regarding one of the coefficients B and C as zero in this manner, calculation can be simplified and the calculation speed can be increased. In addition, since the number of coefficients to be determined is 1, coefficient calculation can be stabilized.

Second Embodiment

Figure 10:
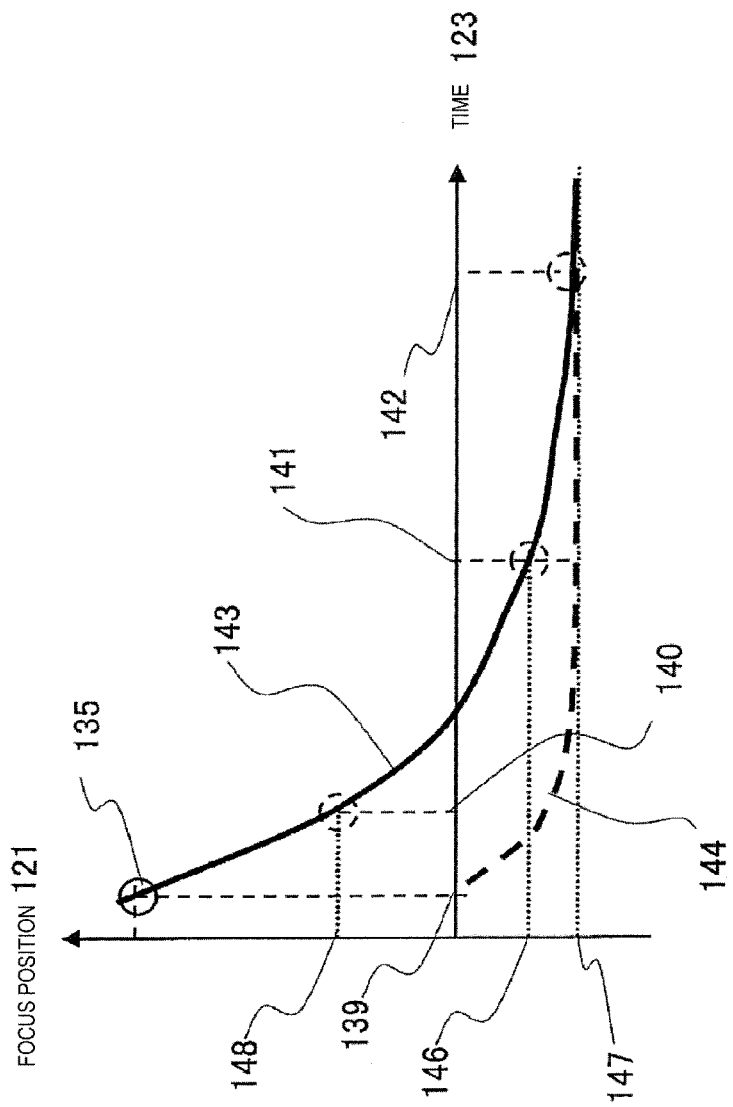
FIG. 10 is an explanatory diagram showing an example of a method of estimating the amount of focus shift.

In the first embodiment, the case has been described in which the time constant (τ$_2$ in expression (2)) of attenuation of a component in which the influence of the change in the support rod 305, that is, the influence of single X-ray irradiation does not occur immediately or a component less influenced by single X-ray irradiation is taken into consideration. However, a second embodiment is a case where the focus shift due to the change in the support rod 305 is very slow compared with the focus shift within the X-ray tube 101 and it can be regarded that the focus shift due to the change in the support rod 305 is constant while X-rays are not irradiated within a predetermined time. This predetermined time is a time at which a focus position change due to the support rod 305 when no X-rays are irradiated changes by the approximate target accuracy in focus control. Hereinafter, the second embodiment will be described with reference to FIG. 10. FIG. 10 is an explanatory diagram showing an example of a method of estimating the amount of focus shift.

The function used in the estimation in this case is expression (9) instead of expression (2), and the coefficients B and C are calculated as in the first embodiment. The explanation will be given with reference to FIG. 9. The coefficient C indicating the amount of change in the support rod 305 is calculated using the detection result 132 in the end stage of the before-last X-ray irradiation and the detection result 133 in the last initial stage, and is expressed as in expression (10). In addition, the coefficient B indicating the focus shift within the X-ray tube 101 is calculated from the coefficient C determined previously and the detection result 134 in the last end stage, and is expressed as B in expression (10). Therefore, the estimated value y(tm) can be described as in expression (11).

$$y = B\exp\left(-\frac{t}{\tau_1}\right) + C \quad \text{Expression (9)}$$

$$C = \frac{yB(n) - yE(n-1)\exp\left(-\frac{tB(n) - tE(n-1)}{\tau_1}\right)}{1 - \exp\left(-\frac{tB(n) - tE(n-1)}{\tau_1}\right)} \quad \text{Expression (10)}$$

$$B = yE(n) - C = $$

$$yE(n) - \frac{yB(n) - yE(n-1)\exp\left(-\frac{tB(n) - tE(n-1)}{\tau_1}\right)}{1 - \exp\left(-\frac{tB(n) - tE(n-1)}{\tau_1}\right)}$$

$$y(tm) = \quad \text{Expression (11)}$$

$$\left[yE(n) - \frac{yB(n) - yE(n-1)\exp\left(-\frac{tB(n) - tE(n-1)}{\tau_1}\right)}{1 - \exp\left(-\frac{tB(n) - tE(n-1)}{\tau_1}\right)}\right]$$

$$\exp\left(-\frac{tm - tE(n)}{\tau_1}\right) +$$

$$\frac{yB(n) - yE(n-1)\exp\left(-\frac{tB(n) - tE(n-1)}{\tau_1}\right)}{1 - \exp\left(-\frac{tB(n) - tE(n-1)}{\tau_1}\right)}$$

In this case, when a longer time than the change in the support rod 305 has passed from the X-ray irradiation, it can not be regarded that the focus shift due to the support rod 305 is constant. Therefore, it is desirable to provide means for resetting the change in the support rod 305 to a predetermined position, for example, the initial focus position, that is, means for replacing the coefficient C in expression (9) with zero.

As another method, when the change in the support rod 305 is very slow, the change in the support rod 305 may be slowly brought close to zero from the last X-ray irradiation, compared with the focus shift within the X-ray tube 101. That is, the coefficient C in expression (9) may be brought close to zero with a large time constant or at low speed. In addition, the coefficient C may be gradually brought close to zero every fixed time.

Although the coefficient C of the present embodiment is determined using the focus position detection result in the initial stage of the last X-ray irradiation, this is an example and does not limit the present invention. For example, the coefficient C may be easily determined using focus position results measured in the initial stages of the past various X-ray irradiations. For example, as described in the first embodiment, the detection result value in the initial stage of the latest X-ray irradiation may be determined as a value of the coefficient C using the data when the X-ray irradiation interval is long enough to reduce the focus shift within the X-ray tube 101, that is, using the data when the term (first term on the right side) of the coefficient B in expression (9) can be regarded as zero.

As another method, for example, when the direction of the focus shift within the X-ray tube 101 and the direction of the change in the support rod 305 are opposite and the direction of the change in the support rod 305 is assumed to be negative, the coefficient C may be determined using the smallest value (largest to the negative side) of the focus position. The effect of this method will be described using with reference to FIG. 10.

In FIG. 10, a circle 135 shows a result when there is X-ray irradiation and accordingly heating occurs and focus detection is performed simultaneously, and a curve 143 shows a focus position change when performing X-ray irradiation in the end stage at time 139. A dotted line 144 shows a change in the focus position due to the support rod 305. The change in the support rod 305 at time 139 is zero, that is, the coefficient C is zero at time 139 and converges on a value 147 gradually with the passage of time. A sum of the focus shift within the X-ray tube 101 and the change in the support rod 3 is the value 147 at time 142 at which the focus shift within the X-ray tube 101 is sufficiently small.

When X-rays are irradiated to obtain the result of the focus position at time 142, the result value 147 is smaller than the focus position detection value at time 139. Accordingly, the coefficient C is determined by the value 147. Since the influence of the coefficient B is small, this value 147 is a value that reflects the change in the support rod 305 most. Accordingly, the correct value of the coefficient C is obtained.

In addition, when X-rays are irradiated to detect the focus at time 141 before the focus shift within the X-ray tube 101 is sufficiently small, a detection result 146 is similarly smaller than the focus position detection value at time 139. Accordingly, the coefficient C is determined by the value 146. This value 146 is not very accurate compared with the convergence value 147 since the influence of the focus shift within the X-ray tube 101 is included, but is closer to the correct value 147 than the value (zero) obtained at time 139 since the change in the support rod 305 is included in part. Therefore, although not complete, it is possible to slightly improve the accuracy of the value of the coefficient C.

In addition, when X-rays are irradiated to detect the focus at time 140 at which the focus shift within the X-ray tube 101 is a main focus shift, this detection result 148 is larger than the value (zero) obtained at time 139. Accordingly, the coefficient C is determined by the value obtained at time 139. If the value 148 is used in this case, the value 148 is largely distant from the value 139 that is a true value. Accordingly, it is possible to prevent a reduction in the accuracy in this method.

Therefore, the determination accuracy of the coefficient C can be improved by updating the coefficient C using the smallest measurement (detection) focus position.

As a specific method of realizing this, focus positions detected by X-ray irradiation are stored in the storage means of the central processing means 105, and the smallest measurement (detection) result of the focus positions is extracted. In this way, the above can be realized. In addition, it is also possible to store the value of the coefficient C before X-ray irradiation in the storage means of the central processing means 105 and to replace the coefficient C with the value of a result obtained by irradiating X-rays when the result is smaller than the coefficient C.

However, when a very long time has elapsed, the change in the support rod 305 also converges on zero. Accordingly, it is desirable to determine the coefficient C using the past data within a predetermined time from the time at which focus estimation is performed.

Third Embodiment

Figure 11:
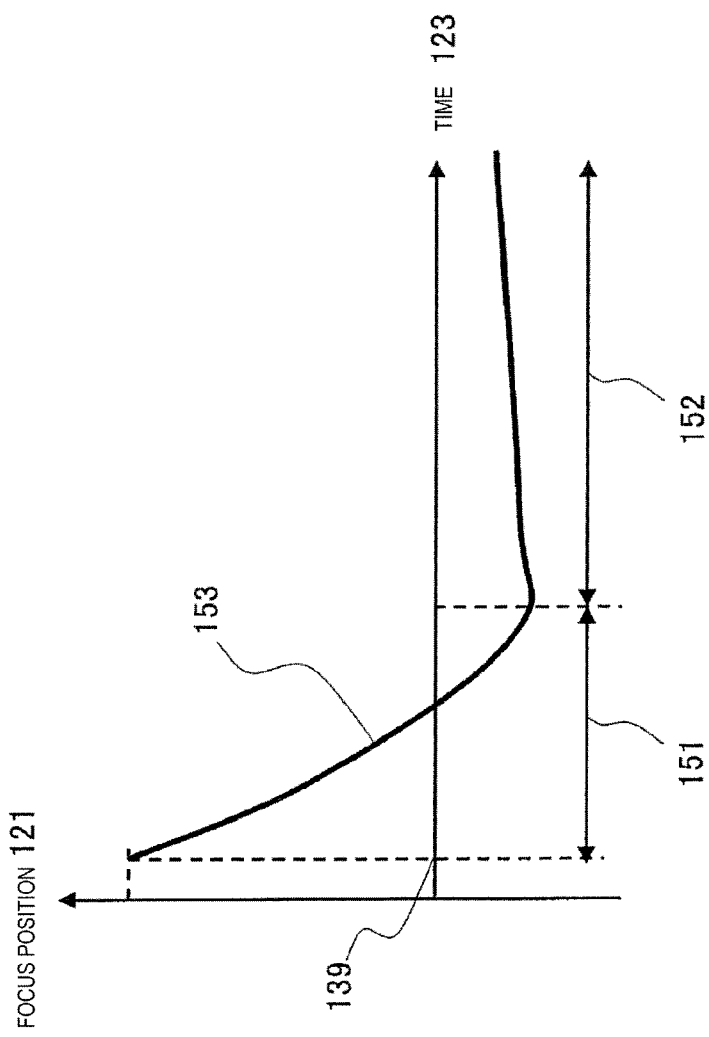
FIG. 11 is a graph showing an example of the focus position evaluation result at the time of cooling of an X-ray tube.
Figure 12:
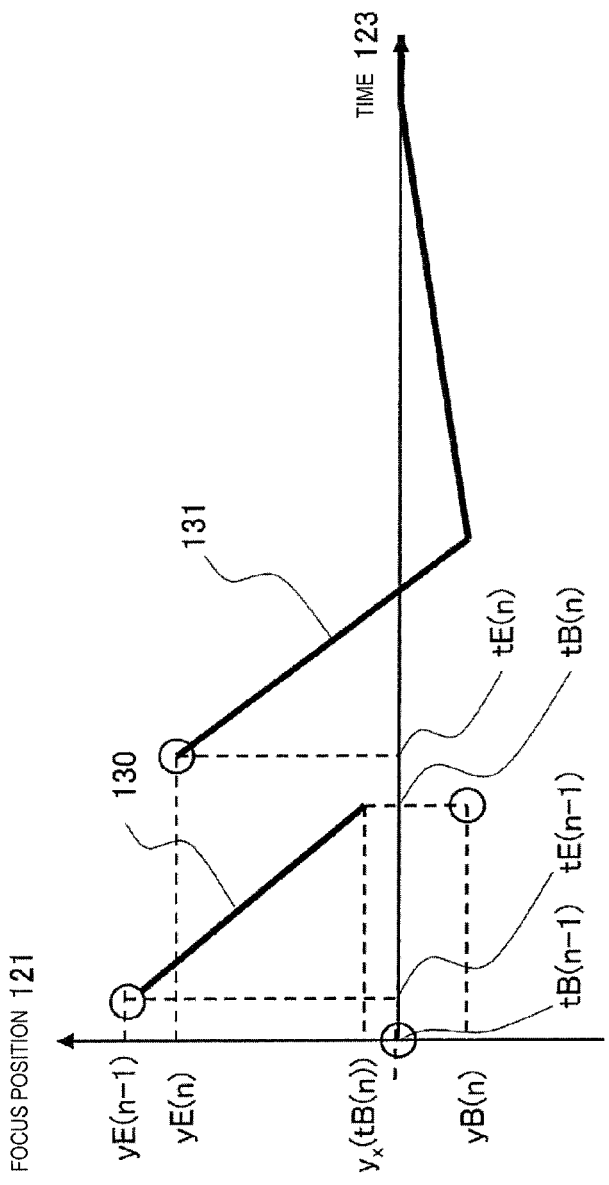
FIG. 12 is an explanatory diagram showing an estimation function determination method of a third embodiment.

Although the case where the time constant is used as a characteristic parameter has been described in the first embodiment, the present embodiment is different from the first embodiment in that the moving speed is used. A focus position control method of the present embodiment will be described with reference to FIGS. 11 and 12. FIG. 11 is a graph showing an example of the focus position evaluation result at the time of cooling of an X-ray tube. FIG. 12 is an explanatory diagram showing an estimation function determination method of the third embodiment.

FIG. 11 shows an example of the focus position evaluation result when the X-ray tube 100 is cooled after being heated by X-rays. A curve 153 is an example of the evaluation result, and the vertical axis indicates the focus position 121 and the vertical axis indicates the elapsed time 123 from the end of X-ray irradiation. It is necessary to perform evaluation and acquire this result in advance of actual imaging. In a period 151, the focus shift within the X-ray tube 101 and the focus shift due to the change in the support rod 305 occur simultaneously. In a period 152, the focus shift due to the change in the support rod 305 mainly occurs. The present embodiment is a case where the focus shift within the X-ray tube 101 and the focus shift due to the change in the support rod 305 occur in the opposite directions.

First, from the result of the curve 153, the speed of focus change in each of the periods 151 and 152 is calculated. In this determination method, for example, a straight line is determined from the data of the period 151 using the least square method, and the inclination is set to the speed $v_1$ in the period 151. The speed obtained at this time is an average speed. Similarly, a speed $v_2$ is determined from the data of the period 152 using the least square method, for example. The speed $v_1$ and the speed $v_2$ determined in this manner are stored in the storage means of the central processing means 105.

Next, the control method will be described. As shown in expression (12), assuming that the time of the end stage of the last X-ray irradiation is zero of time t, the focus position y(t) at time t moves at the speed $v_1$ until time $t_1$, moves at the speed $v_2$ between time $t_1$ and time $t_2$, and stops at the position of zero after time $t_2$. Here, the coefficient D indicates the amount of focus shift within the X-ray tube 101 at time zero, and the coefficient F indicates the amount of focus shift due to the change in the support rod 305 at time zero.

$$\begin{cases} y(t) = D + v_1 t & (0 \leq t \leq t_1) \\ y(t) = F + v_2 t & (t_1 < t \leq t_2) \\ y(t) = 0 & (t > t_2) \end{cases} \quad \text{Expression (12)}$$

The determination method of expression (12), that is, a method of determining the coefficients D and F and the time $t_1$ and $t_2$ will be described with reference to FIG. 12. This is a case where (n−1)-th X-ray irradiation is performed in a state where the X-ray tube is sufficiently cooled and n-th X-ray irradiation is performed before the X-ray tube 101 is cooled. After the (n−1)-th X-ray irradiation, a change in the support rod 305, which is an example of a component in which the influence of single X-ray irradiation does not occur immediately or a component less influenced by single X-ray irradiation, slightly occurs. In FIG. 12, the vertical axis 121 indicates a focus position, the horizontal axis 123 indicates time, and a circle (O) indicates a focus position obtained by performing X-ray irradiation. For the focus position 121, a position without thermal expansion is zero.

In the case of the estimation function 130, since there is no X-ray irradiation before time tB (n−1), there is no focus shift due to the change in the support rod 305 in advance. For this reason, the coefficient F is zero. In addition, since all changes at time tE(n−1) occur due to the focus shift within the X-ray tube 101. For this reason, the coefficient D is yE(n−1). In addition, after tE(n−1), the focus shift within the X-ray tube 101 moves at the fixed speed $v_1$ to reach zero. Accordingly, since the time $t_1$ and the time $t_2$ are equal, they can be described as shown in expression (13).

$$t_1 = t_2 = -\frac{D}{v_1} = -\frac{yE(n-1)}{v_1} \quad \text{Expression (13)}$$

The estimation function 131 is between the (n−1)-th X-ray irradiation and the n-th X-ray irradiation, and a difference between the estimated focus position $y_x(tB(n))$ at time tB(n) when it is assumed that there is no change in the support rod 305 and a focus position detection result yB(n) at the same time is the change in the support rod 305. Therefore, the coefficient F can be written as in expression (14) when a change during the elapsed time (tE(n)−tB(n)) in the initial stage and the end stage of the n-th X-ray irradiation is taken into consideration. Here, when the time of the n-th X-ray irradiation is short, tE(n)=tB(n) may be regarded.

$$F = yB(n) - y_x(tB(n)) - v_2(tE(n) - tB(n)) \quad \text{Expression (14)}$$

In addition, the coefficient D is equal to yE(n). This is because the focus position detection result yE(n) at time tE(n) is determined so as to satisfy expression (12).

In addition, the time $t_1$ is a time at which a change from the focus shift within the X-ray tube 101 to the focus shift due to the change in the support rod 305 occurs, and is a time at which first and second expressions of expression (12) intersect. In addition, the time $t_2$ is a time at which the focus shift due to the change in the support rod 305 becomes zero, and is a time at which the left side of the second expression of expression (12) becomes zero. Therefore, the time $t_1$ and $t_2$ can be written as in expression (15).

$$\begin{cases} t_1 = \dfrac{D-F}{v_2 - v_1} = \dfrac{yE(n) - yB(n) + y_x(tB(n)) + v_2(tE(n) - tB(n))}{v_2 - v_1} \\ t_2 = -\dfrac{F}{v_2} = \dfrac{-yB(n) + y_x(tB(n)) + v_2(tE(n) - tB(n))}{v_1} \end{cases} \quad \text{Expression (15)}$$

The focus position can be estimated by determining the travel time at each speed as described above.

In the present embodiment, a difference between the estimated focus position $y_x(tB(n))$ at time tB(n) when it is assumed that there is no change in the support rod 305 and the focus position detection result yB(n) at the same time is used in the calculation of the coefficient F. However, this does not limit the present invention. For example, only a result may be used when a change in the support rod 305 is a main cause in the focus position detection result yB(n), such as when a predetermined time period has passed from the last X-ray irradiation or when the detected position yB(n) becomes a predetermined value. Here, the predetermined time is a time taken for the thermal expansion in the X-ray tube 101 to converge, and the predetermined value is equal to or less than the initial focus position (zero), for example, in FIG. 12.

Although the travel time $t_1$ and $t_2$ is determined in the present embodiment, this does not limit the present invention. For example, a movement limit position may be determined. As a preferable method, for example, in FIG. 12, the focus position moves at the speed $v_1$ up to the threshold value Lx(t)

after X-ray irradiation and then moves at the speed $v_2$ up to the initial focus position after reaching the threshold value. Since this threshold value Lx(t) can be calculated from the second express ion of expression (12), the threshold value Lx(t) can be written as in expression (16).

$$Lx(t)=F+v_2 t \qquad \text{Expression (16)}$$

In addition, in this case, if the magnitude of the speed $v_2$ is very small, it may be regarded that the threshold value Lx(t) is almost fixed. In this case, since the threshold value Lx(t) is consistent with the coefficient F, the speed $v_2$ is zero. Preferably, the coefficient F is a value of the largest focus position in a direction of the change in the support rod 305 among the focus positions detected within a predetermined time. That is, it is preferable that the focus position move at the speed $v_1$ up to the threshold value, which is determined from the focus detection result within a predetermined time before the last X-ray irradiation, after the X-ray irradiation and then stop. When there is no X-ray irradiation for a predetermined time, resetting is performed as described in the second embodiment, for example. By using the limit position determined in this manner, it is possible to easily determine the focus position.

Fourth Embodiment

Figure 13:
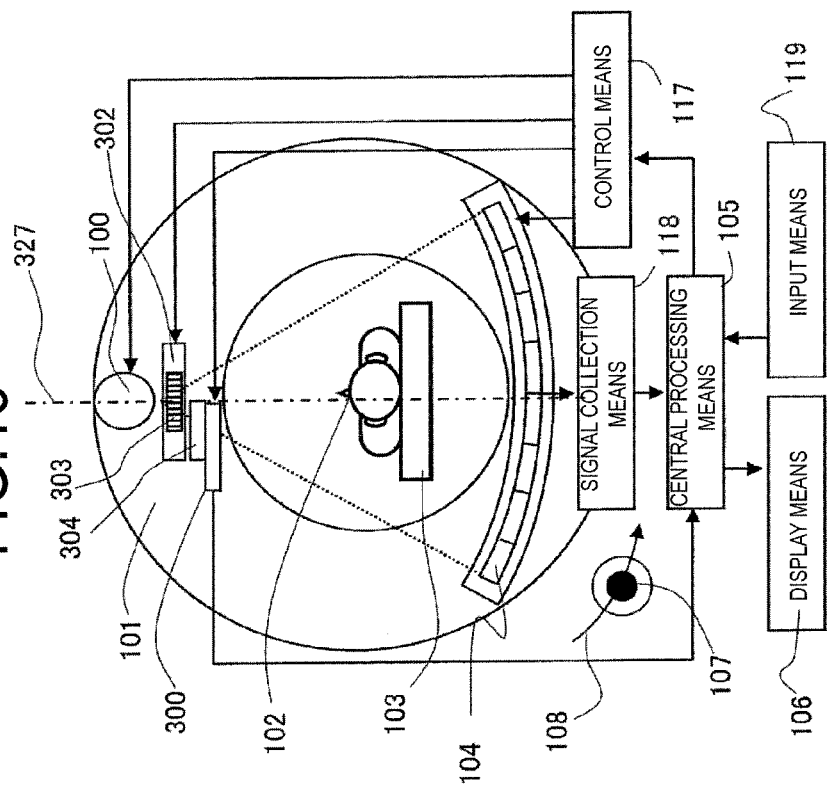
FIG. 13 is a schematic diagram of an X-ray CT apparatus according to a fourth embodiment.
Figure 14:
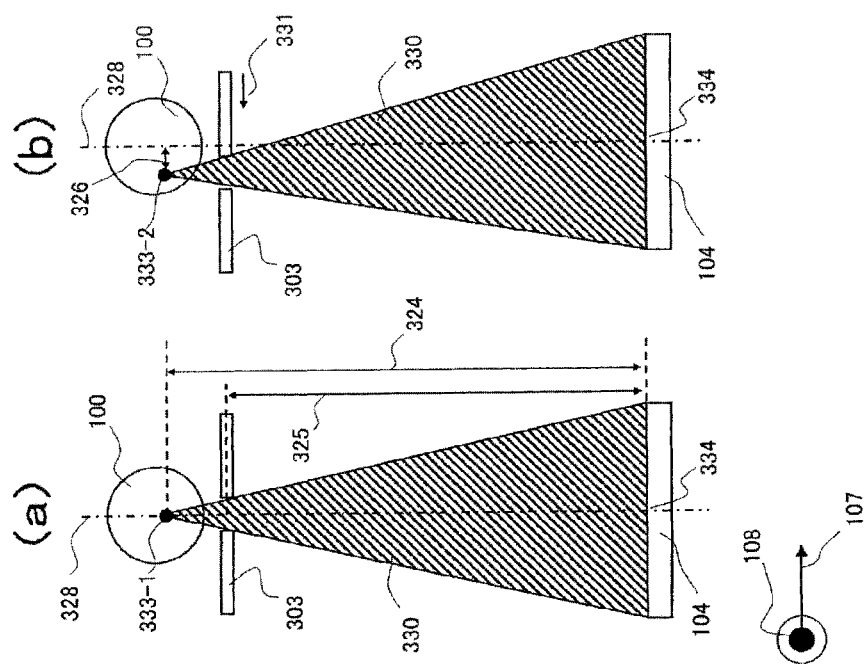
FIG. 14 is an explanatory diagram showing a method of moving an X-ray collimator 303, where

An X-ray CT apparatus of a fourth embodiment is different from that of the first embodiment in that a change in the range of irradiation to the X-ray detector 104 is suppressed by controlling the X-ray collimator 303, which limits the X-ray irradiation range, instead of controlling the X-ray irradiation range by moving the X-ray tube 100. An example of the X-ray CT apparatus of the fourth embodiment will be described with reference to FIGS. 13 and 14. FIG. 13 is a schematic diagram of the X-ray CT apparatus according to the fourth embodiment. FIG. 14 is an explanatory diagram showing a method of moving the X-ray collimator 303. FIG. 14(a) shows a state before focus shift, and FIG. 14(b) shows a case where focus shift occurs due to the heat generated by X-ray irradiation but focus shift control is not performed.

As shown in FIG. 13, this X-ray CT apparatus has X-ray collimator moving means 302 for moving the X-ray collimator 303 in the slice direction 107, and the control means 117 controls the X-ray irradiation region by controlling the X-ray collimator moving means 302. This movement is performed so that the X-ray irradiation region, which is realized by the movement of the X-ray tube 100 in the first embodiment, is similarly realized. In this case, control is performed such that the relationship of expression (17) between the amount of controlled movement Y of the X-ray collimator 303 in the present embodiment and the amount of movement X of the X-ray tube 100 in the focus position control performed in the first embodiment is satisfied.

$$Y=-\frac{S}{T}X \qquad \text{Expression (17)}$$

Here, the references of the X-ray tube movement amount X and the amount of controlled movement Y are set such that both the X-ray tube movement amount X and the amount of controlled movement Y are zero when there is no thermal expansion due to X-rays. In addition, T is a distance (324 in FIG. 14) from the X-ray detector 104 to the focus 333, and S is a distance (325 in FIG. 14) from the X-ray detector 104 to the X-ray collimator 303.

Expression (17) will be described with reference to FIG. 14. FIG. 14 is the X-ray tube 100, the X-ray collimator 303, and the X-ray detector 104 on the cross section of a position 327 in FIG. 13, and a region 330 is an X-ray irradiation region. FIG. 14(a) is before focus shift, and a straight line 328 is a straight line connecting a focus position 333-1 when there is no thermal expansion due to X-rays and the slice center 334 of the X-ray detector 104 in a predetermined irradiation region. FIG. 14(b) is a case where focus shift occurs due to the heat generated by X-ray irradiation but focus shift control is not performed, and a focus 333-2 is located at the position separated from the straight line 328 by a distance 326 in the slice direction 107. Here, since the focus moves by X in a direction opposite to the movement direction of the focus 333-2 in the first embodiment, this distance 326 is −X.

Next, a case where the same predetermined irradiation region as in FIG. 14(a) is realized in FIG. 14(b) will be considered.

In this case, the slice center of the X-ray detector 104 in the actual irradiation region is preferably set to the position 334, and it is preferable to move the X-ray collimator 303 by a distance obtained by multiplying the amount of movement X by the term of a difference in expansion rate due to a difference between the distance from the X-ray detector 104 to the focus 333 and the distance from the X-ray detector 104 to the X-ray collimator 303. The term of the difference in expansion rate is obtained by dividing a distance T (325) between the X-ray detector 104 and the X-ray collimator 303 by a distance S (324) between the X-ray detector 104 and the focus 333-1 or 333-2. Accordingly, it can be seen that it is preferable to move the X-ray collimator 303 in FIG. 14(b) by the amount of movement Y satisfying expression (17).

Here, the reference numeral of expression (17) is negative, and the amount of movement Y and the amount of movement X are in the opposite directions. Therefore, the X-ray collimator 303 moves in the opposite direction to the direction when moving the X-ray tube 100 in the first embodiment, in other words, moves in the same direction as the movement direction of the focus.

By controlling the X-ray collimator 303 as described above, it is possible to control the X-ray irradiation range in the same manner as when controlling the X-ray tube 100 in the first embodiment. As a result, it is possible to eliminate and suppress the degradation of image quality, such as the occurrence of artifacts or a lowering in the quantitative capability due to focus shift.

Fifth Embodiment

Figure 15:
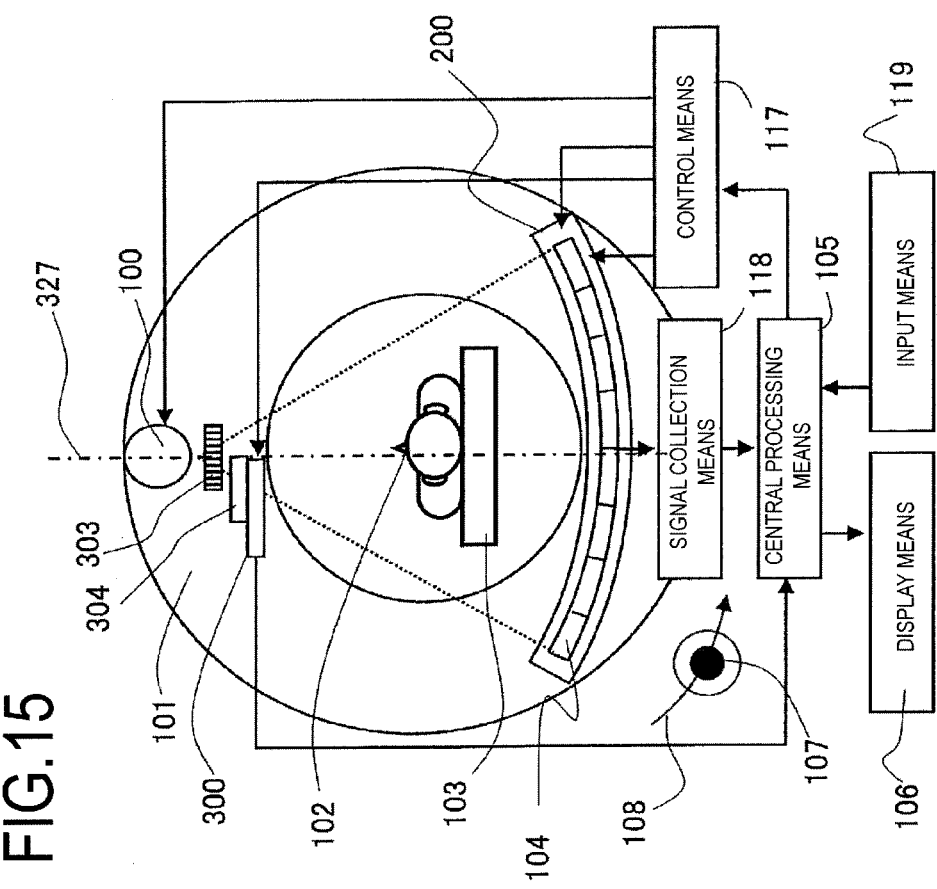
FIG. 15 is a schematic diagram of an X-ray CT apparatus according to a fifth embodiment.
Figure 16:
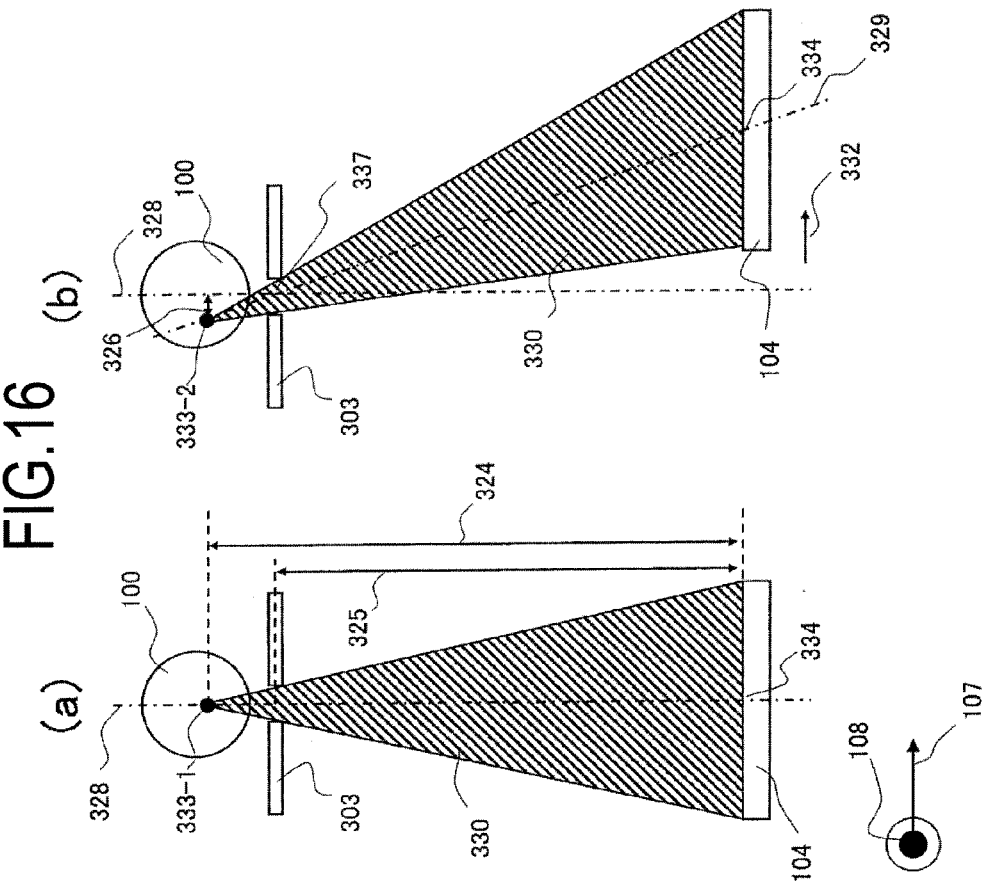
FIG. 16 is an explanatory diagram showing a method of moving an X-ray detector 104, where
Figure 17:
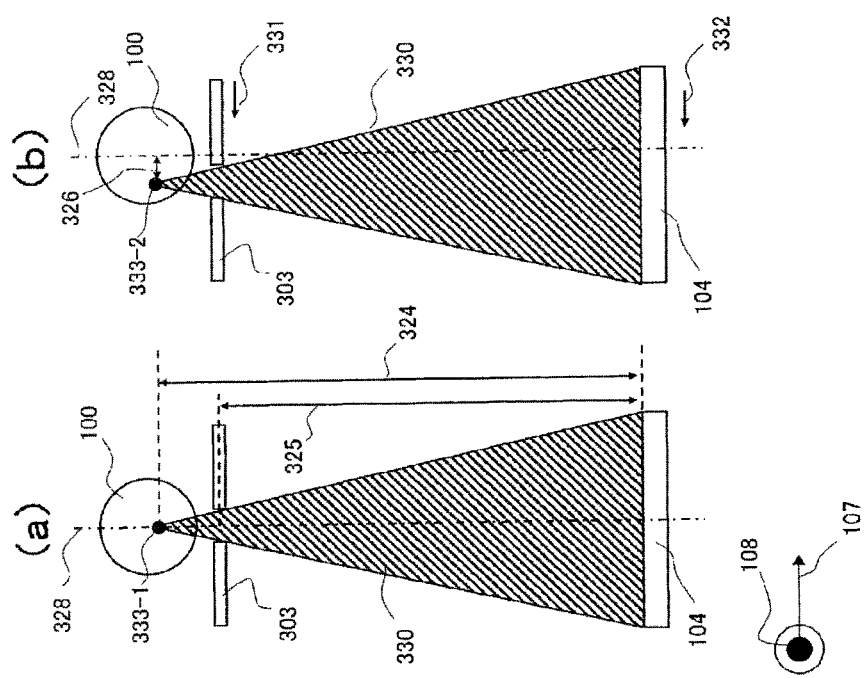
FIG. 17 is an explanatory diagram showing a method of moving the X-ray collimator 303 and the X-ray detector 104, where

An X-ray CT apparatus of a fifth embodiment is different from that of the first embodiment in that, in association with the X-ray irradiation range, the X-ray tube 100 is not controlled according to a change in the focus position but movement control of the position of the X-ray detector 104 is performed so that the range of irradiation to the X-ray detector 104 does not change. An example of the X-ray CT apparatus of the present embodiment will be described with reference to FIGS. 15 to 17. FIG. 15 is a schematic diagram of the X-ray CT apparatus according to the fifth embodiment. FIG. 16 is an explanatory diagram showing a method of moving the X-ray detector 104. FIG. 16(a) shows a state before focus shift, and FIG. 16(b) shows a case where focus shift occurs due to the heat generated by X-ray irradiation but focus shift control is not performed. FIG. 17 is an explanatory diagram showing a method of moving the X-ray collimator 303 and the X-ray detector 104. FIG. 17(a) shows a state before focus shift, and FIG. 17(b) shows a case where focus shift occurs due to the heat generated by X-ray irradiation but focus shift control is not performed.

As shown in FIG. 15, the X-ray CT apparatus according to the present embodiment has X-ray detector moving means 200 for moving the X-ray detector 104 in the slice direction 107, and the control means 117 controls the X-ray irradiation region by controlling the X-ray detector moving means 200. This movement is performed so that the X-ray irradiation region, which is realized by the movement of the X-ray tube 100 in the first embodiment, is similarly realized. In this case, control is performed such that the relationship of expression (18) between the amount of controlled movement Z of the X-ray detector 104 in the present embodiment and the amount of movement X of the X-ray tube 100 in the focus position control performed in the first embodiment is satisfied.

$$Z = \frac{S}{T-S} X \quad \text{Expression (18)}$$

Here, the references of the X-ray tube movement amount X and the amount of controlled movement Z are set such that both the X-ray tube movement amount X and the amount of controlled movement Z are zero when there is no thermal expansion due to X-rays. In addition, T is a distance (324 in FIG. 16) from the X-ray detector 104 to the focus 333, and S is a distance (325 in FIG. 16) from the X-ray detector 104 to the X-ray collimator 303. Expression (18) will be described with reference to FIG. 16. FIG. 16 is the X-ray tube 100, the X-ray collimator 303, and the X-ray detector 104 on the cross section of the position 327 in FIG. 15, and a region 330 is an X-ray irradiation region. FIG. 16(*a*) is before focus shift, and a straight line 328 is a straight line connecting a focus position 333-1 when there is no thermal expansion due to X-rays and the slice center 334 of the X-ray detector 104 in a predetermined irradiation region in the state of FIG. 16(*a*). FIG. 16(*b*) is a case where focus shift occurs due to the heat generated by X-ray irradiation but focus shift control is not performed, and a focus 333-2 is located at the position separated from the straight line 328 by a distance 326 in the slice direction 107. Here, since the focus moves by X in a direction opposite to the movement direction of the focus 333-2 in the first embodiment, this distance 326 is −X.

A case where the same predetermined irradiation region as in FIG. 16(*a*) is realized in FIG. 16(*b*) will be considered. In this case, the slice center position 334 of the irradiation region is preferably on a straight line 329 passing through a point 337 of the intersection of the straight line 328 and the X-ray collimator 303 and the focus 333-2. Therefore, the amount of movement Z of the X-ray detector 104 is a distance obtained by multiplying the position X of the focus position by the ratio between the distance from the X-ray collimator 303 to the X-ray detector 104 and the distance from the X-ray collimator 303 to the focus 333. As a result, it can be seen that the amount of movement Z of the X-ray detector 104 is expressed as in expression (18). Here, the reference numeral of expression (18) is the same, and the amount of movement Z and the amount of movement X are in the same direction. Therefore, the X-ray detector 104 moves in the same direction as when moving the X-ray tube 100 in the first embodiment, in other words, moves in the opposite direction as the movement direction of the focus.

By controlling the X-ray detector 104 as described above, it is possible to control the X-ray irradiation range in the same manner as when controlling the X-ray tube 100 in the first embodiment. As a result, it is possible to eliminate and suppress the degradation of image quality, such as the occurrence of artifacts or a lowering in the quantitative capability due to focus shift.

Although the case where only the X-ray detector 104 is moved has been described in the present embodiment, this is an example and does not limit the present invention. Two or more of the X-ray tube 100, the focus position itself, the X-ray collimator 303, and the X-ray detector 104 may be moved using two or more methods together among the method when moving the X-ray tube 100 or moving the focus position using an electrical field or a magnetic field as described in the first embodiment, the method when moving the X-ray collimator 303 as described in the second embodiment, and the method when moving the X-ray detector 104 as described in the present embodiment. As an example of such a movement method, both the X-ray collimator 303 and the X-ray detector 104 are moved with respect to the focus shift 326 in FIG. 17, for example. FIG. 17(*a*) is a state before focus shift, and focus shift occurs due to the heat generated by X-ray irradiation in FIG. 17(*b*). In this case, it is preferable that the amount of movement Y of the X-ray collimator 303 and the amount of movement Z of the ray detector 104 be the same amount as the amount of movement of the focus in the same direction as the amount of movement of the focus. That is, it is preferable to set the amount of movement X and the amount of movement Z to the same amounts as the amount of movement X of the X-ray tube 100 and the amount of movement X of the focus in the opposite directions to the amount of movement X of the X-ray tube 100 and the amount of movement X of the focus described in the first embodiment.

By performing control in this manner, it is possible to prevent X-rays from being incident on the X-ray detector 104 at a large angle or to prevent a large change in the incidence angle. When an X-ray is obliquely incident on a scintillator at a large angle, one X-ray photon may be detected by a plurality of scintillator elements. As a result, the output characteristics of the X-ray detector 104 may be changed. In addition, if the incidence angle is significantly changed, when the X-ray detector 104 has an X-ray grid in the slice direction, the X-ray grid may make a shadow on the X-ray detection element 228 of the X-ray detector 104. For this reason, X-ray utilization efficiency is reduced. In addition, since the size of the shadow changes due to variations in the position of the X-ray grid, a variation in the output of the X-ray detection element 228 occurs. This may cause the occurrence of artifacts or a lowering in the quantitative capability. In this method, it is possible to suppress these.

Sixth Embodiment

Figure 18:
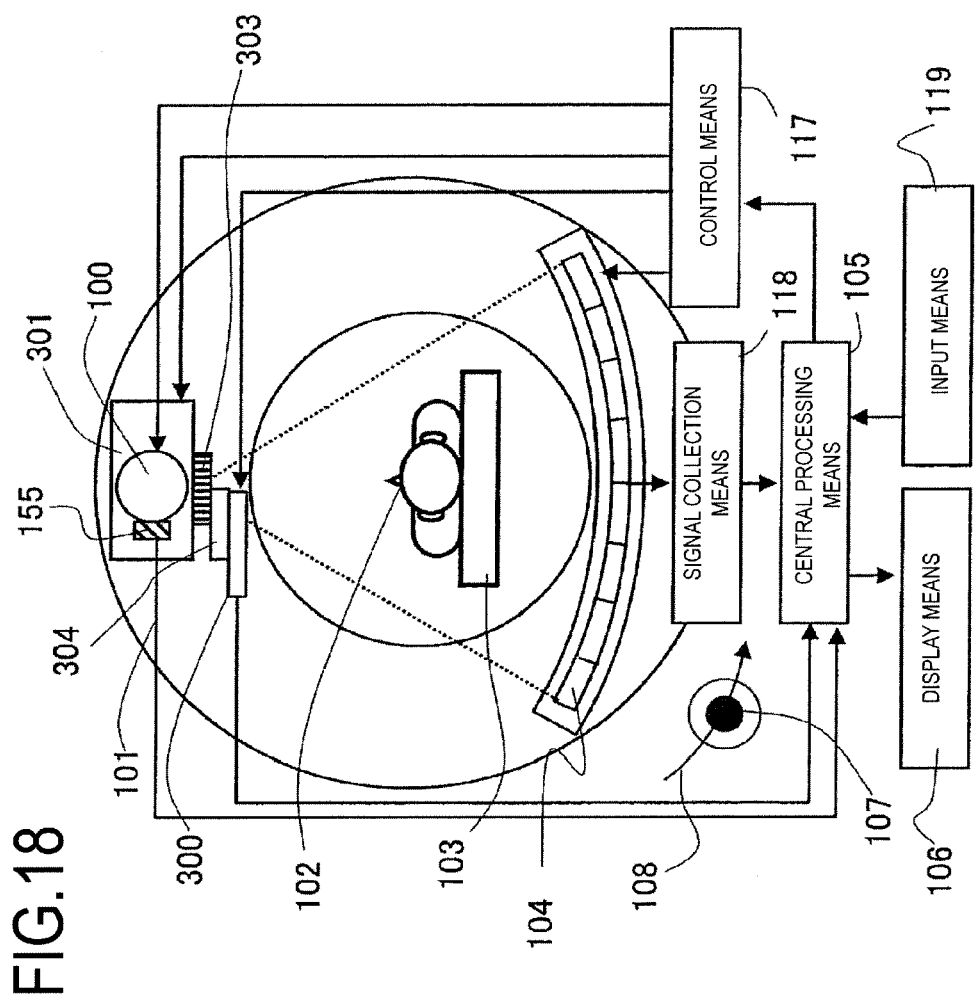
FIG. 18 is a schematic diagram of an X-ray CT apparatus according to a sixth embodiment.

Although the case where the focus shift due to the change in the support rod 305 is determined using the focus position detected by the before-last X-ray irradiation has been described in the first embodiment, an X-ray CT apparatus of the present embodiment is different from that of the first embodiment in that the focus shift due to the change in the support rod 305 is estimated using the temperature around the outside of the X-ray tube 100. This is a case where thermal-expanded some members in which the influence of single X-ray irradiation on the support rod 305 or the like does not occur immediately or thermal-expanded some members less influenced by single X-ray irradiation are provided around the outside of the X-ray tube 100, the members become slowly warm by an increase in the temperature of the X-ray tube due to X-ray irradiation, and the members expand and contract slowly. This is possible since the amount of change (the amount of thermal expansion) is correlated with the temperature around the outside of the X-ray tube 100. An example of the X-ray CT apparatus of the present embodiment will be described with reference to FIG. 18. FIG. 18 is a schematic diagram of the X-ray CT apparatus according to the sixth embodiment.

As shown in FIG. 18, the X-ray CT apparatus of the present embodiment has temperature determination means 155 near the X-ray tube 100. For example, the temperature determination means 155 is a thermometer, such as a thermocouple, a resistance thermometer, or a radiation thermometer. In particular, it is desirable to measure the temperature of the support rod 305 or the temperature near the support rod 305.

A focus control method in the present embodiment will be described. Although the flow of the focus control method is the same as that described in the first embodiment with reference to FIG. 3, measuring the temperature using the temperature determination means 155 in the focus position detection processing of step S2 and the focus shift amount estimation processing of step S7 in FIG. 3 and the method of the focus shift amount estimation processing (step S7) are different. In this focus shift amount estimation processing according to the present embodiment (step S7 in FIG. 3), a focus position is calculated using expression (19), for example.

Here, the time constant $\tau_1$ indicates a time constant of the focus shift within the X-ray tube 101 at the time of cooling, which occurs after heating due to X-ray irradiation, as in the first embodiment. In addition, t indicates an elapsed time after X-ray irradiation, the coefficient B indicates the amount of change in the focus shift within the X-ray tube 101 at time zero, the function f(T) indicates the amount of thermal expansion of the support rod 305 at temperature T, and $T_x$ indicates a temperature measured by the temperature determination means 155 when performing the focus shift amount estimation processing (step S7 in FIG. 3).

$$y = B\exp\left(-\frac{t}{\tau_1}\right) + f(T_x) \quad \text{Expression (19)}$$

Among these, the time constant $\tau_1$ and the function f(T) are determined in advance of actual imaging and are stored in the storage means of the central processing means 105. The time constant $\tau_1$ is determined by measuring the focus position without irradiating X-rays for heating in a state where the X-ray tube is warm, as in the first embodiment, and performing fitting for the result. The function f(T) is obtained by acquiring the relationship between the measurement result of the temperature determination means 155 and the amount of focus shift due to the change in the support rod 305 and by performing fitting for the data. The function f(T) is a polynomial of temperature, for example. When acquiring this relationship, it is desirable to acquire it when the focus shift within the X-ray tube 101 is so small as to be negligible. However, the above can be realized by measuring the change in the focus position and the temperature of the support rod 305 after a time, in which the focus shift within the X-ray tube 100 converges, has approximately passed after the irradiation of X-rays. In addition, in order to obtain the data at a number of temperatures, it is desirable to perform the above while changing the X-ray conditions multiple times because of overheating or changing the temperature of the support rod 305 at the start of overheating.

In actual imaging, for example, as shown in FIG. 9, the focus position is estimated using the focus position yE(n) at X-ray irradiation time tE(n) immediately before estimation, the temperature TE(n) measured by the temperature determination means 155, and the temperature Ttm at time tm at which the estimation is performed. First, the coefficient B indicates the focus shift within the X-ray tube 101 at time zero, and is obtained by excluding the change in the support rod 305 from the detected focus position yE(n). In this case, the amount of change in the support rod 305 can be determined using the temperature TE(n) and the function f(T). Similarly, since the amount of change in the support rod 305 at time tm can be determined using the temperature Ttm and the function f(T), expression (19) can be determined as shown in expression (20).

$$y = (yE(n) - f(TE(n)))\exp\left(-\frac{t}{\tau_1}\right) + f(Ttm) \quad \text{Expression (20)}$$

Since the focus shift due to the change in the support rod 305 can also be taken into consideration by estimating the focus position using the estimation function expression (20) in which such coefficients have been determined, accurate estimation is possible.

Although the case in which determination is performed using the relational expression of the amount of focus shift due to the change in the support rod 305 and the measurement result of the temperature determination means 155 has been described in the present embodiment, this is an example and does not limit the present invention. It is needless to say that the measurement result of the temperature determination means 155 and data itself of the amount of focus shift due to the change in the support rod 305, which are obtained by pre-measurement, may be used.

Although the case where the time constant is used as a characteristic parameter has been described in the present embodiment, this is an example and does not limit the present invention. For example, as described in the third embodiment, it is also possible to use a moving speed. In this case, when determining the estimation function 131 in FIG. 12, an estimated focus position is determined so as to move at the fixed speed $v_1$ until it reaches the amount of change f(Ttm) in the support rod 305 determined by the function f(T) after the focus is detected by X-ray irradiation at time tE(n).

In addition, when this is realized by using the estimation function, for example, expression (21) is used.

$$\begin{cases} y = yE(n) + v_1 t & \left(0 \le t \le \frac{f(Ttm) - yE(n)}{v_1}\right) \\ y = f(Ttm) & \left(t > \frac{f(Ttm) - yE(n)}{v_1}\right) \end{cases} \quad \text{Expression (21)}$$

Here, since f(Ttm) changes with time, it is desirable to perform focus detection and temperature measurement at short intervals of time.

Although the case where the temperature determination means 155 is provided near the support rod 305 has been described in the present embodiment, this is an example and does not limit the present invention. The temperature determination means 155 may be provided at various positions near the X-ray tube 100. In particular, when there is a member which causes a change in the focus position but in which the influence of single X-ray irradiation does not occur immediately or the influence of single X-ray irradiation is small, it is desirable to provide the temperature determination means 155 directly or adjacent to the member.

Although the case where a thermometer is used as the temperature determination means 155 has been described in the present embodiment, this is an example and does not limit the present invention. For example, for the temperature of a member near the X-ray tube 100, such as the support rod 305, the amount of heat emitted by the X-ray tube 100 and the amount of heat escaping from the hot bath may be calculated, and the amount of thermal expansion may be calculated from the result. In this case, the amount of heat emitted by the X-ray tube is calculated from the conditions, such as tube voltage, tube current, and irradiation time in the past X-ray irradiation, for example. The amount of heat escaping from the hot bath is calculated from the performance of the X-ray tube 100 exhausting heat. In addition, the relationship between the amount of heat accumulated in a member and the amount of thermal expansion is evaluated and stored in advance of actual measurement. At the time of calculation, a temperature changed to the amount of heat may be calculated from the calculation.

By using the temperature or the amount of heat calculated as described above, it is possible to perform estimation on the basis of the amount of heat even if the temperature determination means 155 is not added. In addition, in the case of a position at which the temperature of the support rod 305 cannot be measured or when a place change that causes thermal expansion slowly is unknown, the function f(T) can be determined by determining the amount of thermal expansion in this method. Therefore, it is possible to perform accurate estimation in consideration of the focus shift due to the change in the support rod 305.

Other Embodiments

Although the embodiments of the X-ray CT apparatus for medical applications have been described in the first to sixth embodiments, the present invention is not limited thereto, and it is needless to say that the present invention can be applied to all apparatuses in which the X-ray source 100, the focus position detection means, and the irradiation range changing means such as the X-ray tube moving means 301, the X-ray collimator moving means 302, or the X-ray detector moving means 200, which are described in the embodiments, are mounted. As examples, the present invention may be applied to an X-ray CT apparatus for non-destructive inspection, an X-ray cone beam CT apparatus, a dual-energy CT apparatus, an X-ray image diagnosis apparatus, an X-ray imaging apparatus, an X-ray fluoroscope, mammography, a digital subtraction apparatus, a nuclear medicine screening apparatus, a radiotherapy apparatus, and the like.

In addition, the present invention is not limited to the embodiments described above, and various modifications may be made within the scope without departing from the scope and spirit of the present invention in the phase of implementation. In addition, various phases are included in the embodiments described above, and various inventions may be extrapolated by proper combination of the plurality of components disclosed. For example, some components may be deleted from all components shown in the embodiments.

According to the X-ray imaging apparatus according to the present embodiment, when X-ray focus shift occurs due to a plurality of thermal expansion factors of different temperature transmissions, it is possible to accurately determine and change the X-ray irradiation range before aging even if the X-ray irradiation is not performed in order to detect the focus position proximately. As a result, it is possible to eliminate and suppress the degradation of image quality, such as the occurrence of artifacts or a lowering in the quantitative capability due to focus shift, without delaying the imaging timing.

REFERENCE SIGNS LIST

100: X-ray source
101: gantry rotation unit
102: object
103: top panel bed
104: X-ray detector
105: central processing means
106: display means
107: rotation axis direction, slice direction
108: rotation direction, channel direction
110: movement direction
117: control circuit
118: signal collection means
119: input means
120: difference value
121: focus position
122: function
123: time
124, 125: time
127, 128: curve of focus position detection result
130, 131: estimation function
132 to 135: focus detection result
139 to 142: time
143: curve showing focus position change
144: dotted line
146 to 148: detected focus position
151, 152: period
153: curve of focus position evaluation result
155: temperature determination means
200: X-ray-detector moving means
228: X-ray detection element
300: detector for focus position measurement
301: X-ray tube moving means
302: X-ray collimator moving means
303: X-ray collimator
304: slit for focus position measurement
305: support rod
306: focus position detection means
310: X-ray detection element for focus detection
311: connector
312: shadow
324 to 326: distance
327: cross section position
328: straight line connecting focus position 333-1 when there is no thermal expansion due to X-rays and slice center 334 of X-ray detector 104 in predetermined irradiation region
329: straight line passing through focus 333 and point of intersection 337
330: X-ray irradiation region
331, 332: movement direction
333: focus
334: slice center
337: point of intersection of straight line 328 and X-ray collimator 303
400: X-ray target
402: rotation axis of X-ray target
403: rotation axis
404: X-ray irradiation range
405: X-ray

The invention claimed is:

1. An X-ray imaging apparatus comprising:
   an X-ray generation unit that irradiates X-rays from a focus and that has a first portion changing so as to have a first change component and a second portion changing so as to have a second change component, which is different from the first change component, due to heat generated by the X-ray generation unit;
   an X-ray detection unit that detects the X-rays and converts the detected X-rays into electrical signals;
   a focus position detection unit that detects a focus position when the X-rays are irradiated;
   a focus position change amount estimation unit that estimates an amount of change in the focus position with respect to a reference position of the focus using a first amount of change, which changes so as to have the first change component, and a second amount of change, which changes so as to have the second change component; and a correction unit that corrects relative positions of an irradiation region of the X-rays and the X-ray detection unit so as to cancel the amount of change in the focus position estimated by the focus position change amount estimation unit;

wherein the focus position change amount estimation unit estimates the amount of change in the focus position using an estimation function obtained from a sum of a first term for calculating the first amount of change and a second term for calculating the second amount of change;

wherein the first term is defined by one or more attenuation terms using the first change component and a first amplitude term, and the second term is defined by one or more attenuation terms using the second change component and a second amplitude term.

2. The X-ray imaging apparatus according to claim 1, wherein the focus position change amount estimation unit determines the second amplitude term using one or more focus positions detected by the focus position detection unit in an X-ray irradiation period corresponding to a period before immediately before focus position estimation is performed.

3. The X-ray imaging apparatus according to claim 2, wherein the focus position change amount estimation unit determines the second amplitude term using a focus position, which is detected by the focus position detection unit in an end stage of an n-th X-ray irradiation period corresponding to a period before immediately before the focus position estimation is performed, and a focus position, which is detected by the focus position detection unit in an initial stage of an (n+1)-th X-ray irradiation period.

4. The X-ray imaging apparatus according to claim 3, wherein the X-ray imaging apparatus is an X-ray CT apparatus that detects X-rays by performing rotational movement around an object of at least one rotation in a state where the X-ray generation unit and the X-ray detector face each other, and an initial stage and an end stage of the X-ray irradiation period are a time included in a first half and a time included in a second half in one rotation in the rotational movement, respectively, or a time included in a first half and a time included in a second half in a plurality of continuous rotational movements, respectively.

5. The X-ray imaging apparatus according to claim 1, wherein the focus position change amount estimation unit determines the first amplitude term using the second change component and a focus position detected in an end stage of a last X-ray irradiation period.

6. The X-ray imaging apparatus according to claim 5, wherein the X-ray imaging apparatus is an X-ray CT apparatus that detects X-rays by performing rotational movement around an object of at least one rotation in a state where the X-ray generation unit and the X-ray detector face each other, and an initial stage and an end stage of the X-ray irradiation period are a time included in a first half and a time included in a second half in one rotation in the rotational movement, respectively, or a time included in a first half and a time included in a second half in a plurality of continuous rotational movements, respectively.

7. The X-ray imaging apparatus according to claim 1, wherein the focus position change amount estimation unit sets one of the first and second amplitude terms of the estimation function to 0, and calculates the other first amplitude term or the other second amplitude.

8. The X-ray imaging apparatus according to claim 7, wherein the focus position change amount estimation unit sets the second term of the estimation function to 0 and calculates the first amplitude term by applying a focus position, which is detected by the focus position detection unit in an X-ray irradiation period immediately before focus position estimation is performed, to the estimation function, or sets the first term of the estimation function to 0 and calculates the second amplitude term by applying a focus position, which is detected by the focus position detection unit in an X-ray irradiation period before immediately before the focus position estimation is performed, to the estimation function.

9. The X-ray imaging apparatus according to claim 8, wherein the focus position change amount estimation unit determines the second amplitude term using the focus position detected by the focus position detection unit at a point of time when an interval of X-ray irradiation time is long enough so that the first amount of change is regarded as 0.

10. The X-ray imaging apparatus according to claim 1, wherein, when a movement direction of the first change component and a movement direction of the second change component are opposite directions, the focus position change amount estimation unit determines the second amplitude term using a focus position that has moved most largely in the movement direction of the second change component.

11. The X-ray imaging apparatus according to claim 1, wherein the correction unit includes at least one of a unit that moves an X-ray tube provided in the X-ray generation unit in order to cancel the amount of change in the focus position, a unit that moves a position of a collimator that restricts an irradiation region of the X-rays in order to cancel the amount of change in the focus position, a unit that moves the X-ray detection unit in order to cancel the amount of change in the focus position.

12. The X-ray imaging apparatus according to claim 1, further comprising:
a temperature determination unit that determines a temperature of the X-ray generation unit,
wherein the focus position change amount estimation unit determines the second change component from a detection result of the temperature determination unit.

13. An X-ray imaging apparatus comprising:
an X-ray generation unit that irradiates X-rays from a focus and that has a first portion changing so as to have a first change component and a second portion changing so as to have a second change component, which is different from the first change component, due to heat generated by the X-ray generation unit;
an X-ray detection unit that detects the X-rays and converts the detected X-rays into electrical signals;
a focus position detection unit that detects a focus position when the X-rays are irradiated;
a focus position change amount estimation unit that estimates an amount of change in the focus position with respect to a reference position of the focus using a first amount of change, which changes so as to have the first change component, and a second amount of change, which changes so as to have the second change component; and a correction unit that corrects relative positions of an irradiation region of the X-rays and the X-ray detection unit so as to cancel the amount of change in the focus position estimated by the focus position change amount estimation unit;

wherein the focus position change amount estimation unit estimates the amount of change in the focus position using an estimation function obtained from a sum of a first term for calculating the first amount of change and a second term for calculating the second amount of change;

wherein, within a limited time for which the second amount of change is regarded to be constant, the first term is defined by an attenuation term using the first change component and a first amplitude term, and the second term is defined as a constant using a second amplitude term.

14. An X-ray focus position control method of an X-ray imaging apparatus including an X-ray generation unit that irradiates X-rays from a focus and has a first portion changing so as to have a first change component and a second portion changing so as to have a second change component, which is different from the first change component, due to heat generated by the X-ray generation unit and an X-ray detection unit that detects the X-rays and converts the detected X-rays into electrical signals, the method comprising:

(a) a step of detecting a focus position when the X-rays are irradiated;

(b) a step of estimating an amount of change in the focus position with respect to a reference position of the focus using a first amount of change, which changes so as to have the first change component, and a second amount of change, which changes so as to have the second change component; and (c) a step of correcting relative positions of an irradiation region of the X-rays and the X-ray detection unit so as to cancel the estimated amount of change in the focus position, wherein the amount of change in the focus position is estimated in (b) using an estimation function obtained from a sum of a first term for calculating the first amount of change and a second term for calculating the second amount of change, and wherein the first term is defined by one or more attenuation terms using the first change component and a first amplitude term, and the second term is defined by one or more attenuation terms using the second change component and a second amplitude term.

* * * * *